US006835395B1

(12) United States Patent
Semple et al.

(10) Patent No.: US 6,835,395 B1
(45) Date of Patent: Dec. 28, 2004

(54) COMPOSITION CONTAINING SMALL MULTILAMELLAR OLIGODEOXYNUCLEOTIDE-CONTAINING LIPID VESICLES

(75) Inventors: Sean C. Semple, Vancouver (CA); Sandra K. Klimuk, North Vancouver (CA); Troy O. Harasym, Vancouver (CA); Nancy Dos Santos, Richmond (CA); Steven M. Ansell, Vancouver (CA); Pieter R Cullis, Vancouver (CA); Michael J. Hope, Vancouver (CA); Peter Scherrer, Vancouver (CA); Deirdre McIntosh, Vancouver (CA); Kim F. Wong, Vancouver (CA); Norbert Maurer, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 09/654,373

(22) Filed: Sep. 1, 2000

Related U.S. Application Data

(63) Continuation-in-part of application No. 09/078,954, filed on May 14, 1998, now Pat. No. 6,287,591, which is a continuation-in-part of application No. 08/856,374, filed on May 14, 1997, now abandoned.
(60) Provisional application No. 60/152,179, filed on Sep. 2, 1999.

(51) Int. Cl.$^7$ ........................ A61K 9/127; A61K 31/70; C12N 11/02; C12N 15/88; C07H 21/00

(52) U.S. Cl. .................... 424/450; 428/402.2; 435/177; 435/458; 514/44; 536/22.1

(58) Field of Search ...................... 424/450; 428/402.2; 435/177, 458; 514/44; 536/22.1

(56) References Cited

U.S. PATENT DOCUMENTS

| | | | |
|---|---|---|---|
| 5,264,618 A | 11/1993 | Felgner et al. ................. | 514/44 |
| 5,552,155 A | 9/1996 | Bailey et al. ................. | 424/450 |
| 5,595,756 A | 1/1997 | Bally et al. ................... | 424/450 |
| 5,705,385 A | 1/1998 | Bally et al. .............. | 424/320.1 |
| 5,843,742 A | 12/1998 | Natsoulis et al. ........ | 435/172.3 |
| 5,965,542 A | 10/1999 | Wasan et al. ................ | 560/224 |
| 5,998,383 A | 12/1999 | Wright et al. ................. | 514/44 |

FOREIGN PATENT DOCUMENTS

| | | |
|---|---|---|
| WO | WO 96/18372 A2 | 6/1995 |
| WO | WO 95/27478 A1 | 10/1995 |
| WO | WO 96/10390 | 4/1996 |
| WO | WO 96/10391 | 4/1996 |
| WO | WO 96/40964 | 12/1996 |
| WO | WO 97/07784 | 3/1997 |
| WO | WO 97/46223 A1 | 12/1997 |
| WO | WO 97/46671 | 12/1997 |

OTHER PUBLICATIONS

Akhtar, S., et al., Liposome delivery of antisense oligonucleotides: adsortpion and efflux characteristics of phosphorothioate oligodeoxynucleotides; Journal of Controlled Release, 22 (1992) 47–56.
Bennett, C. Frank, Intracellular Delivery of Oligonucleotides with Cationic Liposomes, Chapter 14.
Bennett, C. Frank, et al., Pharmacokinetics in mice of a [$^3$H]–labeled phosphorothioate oligonucleotide formulated in the presence and absence of a cationic lipid; Journal of Controlled Release, 41 (1996) 121–130.
Juliano, R.L. et al., Liposomes as a Drug Delivery System for Antisense Oligonucleotides; Antisense Research and Development 2:165–176 (1992).
Litzinger, David C., Limitations of Cationic Liposomes For Antisense Oligonucleotide Delivery in Vivo, Journal of Liposome Research, 7(1), 51–61 (1997).
Thierry, Alain R., et al., Liposomal Delivery as a New Approach to Transport Antisense Oligonucleotides; Gene Regulation: Biology of Antisens4e RNA and DNA. 1992, pp 147–161.
Zelphati, Oliver, et al., Inhibition of HIV–1 Replication in Cultured Cells with Antisense Oligonucleotides Encapsulated in Immunoliposomes; Antisense Research and Development 3:323–338 (1993).
Zelphati, Oliver, et al., Liposomes as a carrier for intracellular delivery of antisense oligonucleotides: a real or magic bullet? Journal of Controlled Release 41 (1996) 99–119.

(List continued on next page.)

Primary Examiner—David M. Naff
(74) Attorney, Agent, or Firm—Oppedahl & Larson LLP

(57) ABSTRACT

Lipidic compositions with superior characteristics for in vivo delivery of oligodeoxynucleotides (ODN) can easily and efficiently be made in the form of small multilamellar vesicles. The compositions contain a population of nucleic acid-containing lipid vesicles in a liquid carrier, and at least a portion of the lipid vesicles are small multilamellar vesicles. The small multilamellar vesicles are made from a lipid component including 20–30 mol % of an ionizable amino lipid such as DODAP, and a steric barrier lipid such as PEG-CerC$_{14}$; and an oligodeoxynucleotide contained in the lumen or interlamellar spaces of the small multilamellar vesicles. The ODN and lipid components are preferably present in the small multilamellar vesicles in a mole ratio of from 0.15 to 0.25. The compositions of the invention can be made by preparing two solutions: a lipid mixture with 20–30 mol % of the ionizable amino lipid, the steric barrier lipid and additional lipid components selected from among neutral lipids and sterols in an ethanolic solvent; and a solution of oligodeoxynucleotide in an aqueous solvent having a pH at which the ionizable amino lipid is positively charged. The lipid mixture is added to the solution of oligodeoxynucleotide to form a mixture containing lipid vesicles which is then massed through a filter to produce sized lipid vesicles in a solution containing ethanol. The ethanol is then removed, for example by dialysis. Then, the pH of the solution surrounding the sized lipid vesicles is increased to reduce the net positive charge on the exterior of the sized lipid vesicles.

9 Claims, 15 Drawing Sheets

OTHER PUBLICATIONS

Tomita, N., et al., "Transient Decrease in High Blood Pressure by in Vivo Transfer of Antisense Oligodeoxynucleotides Against Rat Angiotensinogen", Hypertension 26(1): 131–136, Jul., 1995.

Thierry, A.R., et al., "Liposome delivery of antisense oligonucleotides: adsorption and efflux characteristics of phosphorothioate oligodeoxynucleotides". Journal of Controlled Release 22(1): 47–56.

Li, et al, "Target Delivery of Antisense Oligodeoxynucleotides by LPDH", J. Liposome Res. 7: 411–430 (1997).

IMMEDIATELY AFTER REMOVAL OF FREE ANTISENSE

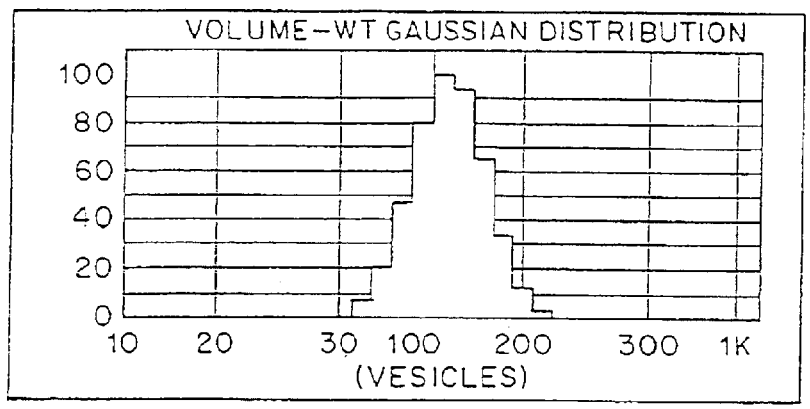

VOLUME WEIGHTING:
MEAN DIAMETER = 119.3 nm
STD DEVIATION = 32.2 nm (27.0 %)
CUMULATIVE RESULTS:
25 % OF DISTRIBUTION < 88.60 nm
50 % OF DISTRIBUTION < 106.74 nm
75 % OF DISTRIBUTION < 127.93 nm
90 % OF DISTRIBUTION < 151.04 nm
99 % OF DISTRIBUTION < 199.22 nm

AFTER 2 MONTH STORAGE AT 4°C

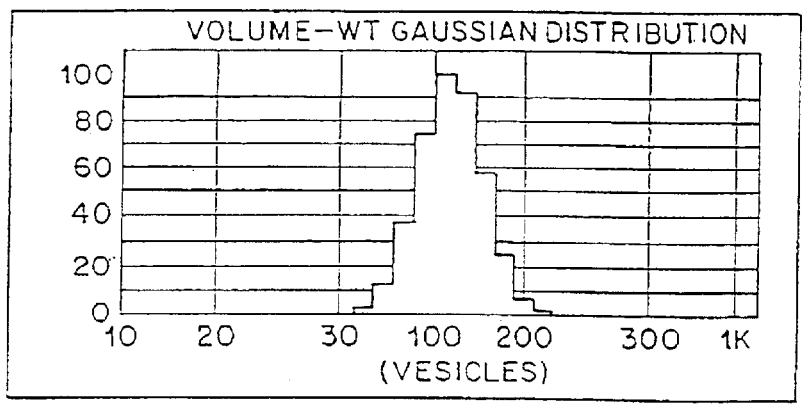

VOLUME WEIGHTING:
MEAN DIAMETER = 114.2 nm
STD DEVIATION = 27.8 nm (24.3 %)
CUMULATIVE RESULTS:
25 % OF DISTRIBUTION < 86.96 nm
50 % OF DISTRIBUTION < 102.86 nm
75 % OF DISTRIBUTION < 121.31 nm
90 % OF DISTRIBUTION < 140.78 nm
99 % OF DISTRIBUTION < 183.74 nm

COMPOSITION CONTAINING SMALL MULTILAMELLAR OLIGODEOXYNUCLEOTIDE-CONTAINING LIPID VESICLES

This application claims priority under 35 U.S.C. § 119(e) from U.S. Provisional Application Ser. No. 60/152,179 filed Sep. 2, 1999, which is incorporated herein by reference. This application is also a continuation-in-part of U.S. patent application Ser. No. 09/078,954, filed May 14, 1998, now U.S. Pat. No. 6,287,591, which is a continuation-in-part of U.S. patent application Ser. No. 08/856,374, filed May 14, 1997, now abandoned, which applications are incorporated herein by reference.

BACKGROUND OF THE INVENTION

This application relates to oligodeoxynucleotide-containing small multilamellar lipid vesicles to methods of making such vesicles.

Oligodeoxynucleotides (ODN), ribozymes and plasmid DNA are recognized as having potential for many therapeutic applications. For example, sequence-specific antisense ODN may be used to inhibit expression of gene sequences. However, these large polyanionic macromolecules possess several inherent characteristics that restrict their pre-clinical and clinical utility for the therapy of chronic diseases. These include (1) the cost and production of clinical grade materials (Prazeres et al., *Trends Biotechnol.* 17: 169–174(1999));
(2) degradation and inactivation by nucleases in plasma and cells (Akhtar et al., *Life Sci.* 49: 1793–801 (1991));
(3) poor intracellular delivery (Hope et al., *Mol. Membr. Biol.* 15: 1–14(1998), Rojanasukul, Y., *Adv. Drug. Delivery Rev.* 118: 115–131 (1996));
(4) rapid plasma elimination (Agrawal and Zhang, *Ciba Found. Symp.* 209: 60–75 (1997), Crooke et al., *J. Pharmacol. Exp. Ther.* 227: 923–937 (1996)); and
(5) renal and dose-limiting hemodynamic toxicities (Henry et al., *J. Pharmacol. Exp. Ther.* 281: 810–816 (1997), Henry et al., *Antisense Nucleic Acid Drug Dev.* 7: 503–510 (1997), Galbraith et al., *Antisense Res. Dev.* 4: 201–206 (1994).

In an effort to overcome these problems, efforts have been made to formulate DNA and RNA-based therapeutics in lipid delivery systems. (Hope, et al., supra, Zelphati, et al., *J. Liposome Res.* 7: 31–49 (1997), Smyth-Templeton, et al., *Nat. Biotechnol.* 15: 647–652 (1997)). The development of such systems has been limited by two principal factors—low encapsulation efficiency (generally <10%) and low drug-to-lipid ratios (0.001–0.1%, w/w) when using neutral lipids. For example, utilization of cationic lipids has been shown to provide improved encapsulation efficiency. Thus, Gokhale et al. (*Gene Ther.* 4: 1289–1299 (1997)) have described a lipid composition of PC:CH:DDAB (55:28:17 molar ratio) containing raf-1 ODN that sensitizes SQ-20B xenografted tumors to ionizing radiation. However, only 1% of the total administered dose remained in the circulation 5 minutes post irradiation.

In other efforts to improve encapsulation efficiencies, several approaches have been employed to entrap antisense ODN in lipid vesicles. For example, the minimum volume entrapment (MVE) procedure described by Thierry et al., (*Nucleic Acids Res.* 20: 5691–5698 (1992), *Gene Regulation: Biology of Antisense RNA and DNA* (Erickson and Izant, eds.), pp. 147–161, Raven Press Ltd, New York (1992)) generates high encapsulation efficiencies and fairly high drug to lipid-ratios. However, the formulation employs 3–7% cardiolipin, which is a potent activator of rat and human complement, thus giving rise in increased hemodynamic toxicity. Furthermore, similar liposome formulations containing cardiolipin have been shown to exhibit very short circulation times. Thus, such compositions overcome some of the problems with free ODN therapeutics only at the expense of increasing other problems. The clinical application of this formulation of such compositions would therefore be expected to be limited. (Chonn, et al., *J. Biol. Chem*/267: 18759–18765 (1992).

Another approach to improving encapsulation efficiency has been to chemically modify the ODN to make them more lipophilic. (Juliano and Akhtar, *Antisense Res. Dev.* 2: 165–176 (1992), Tari et al, *Blood* 84: 4601–4607 (1994). However, these molecules are insoluble in aqueous environments which has, at least until recently, placed limitations on their clinical development. (See Tari et al., *J. Liposome Res.* 8: 251–264 (1998)).

What these and similar studies clearly establish is that the interaction of anionic ODN and lipid carriers with the body is a very complicated one, which cannot be readily predicted. These and similar studies also show that there remains substantial room for improvement in such compositions in order to avoid the various drawbacks described above.

International Patent Publication No. WO 96/40964 discloses several methods for making lipid-nucleic acid particles One of these methods involves preparing a mixture of cationic and non-cationic lipids in an organic solvent, contacts and aqueous solution of nucleic acid with said mixture to provide a clear single phase, and removing the organic solvent. The list of organic solvent on Page 26 of this publication does not include ethanol, the solvent used in the present invention. Furthermore, electron microscopic observation of the lipid particles formed in this methodology shows that they are large unilamellar vesicles (See example 8 of WO 96/40964), and thus that they are structurally different from the compositions of the present invention.

SUMMARY OF THE INVENTION

It has now been determined that lipidic compositions with superior characteristics for in vivo delivery of oligodeoxynucleotides can easily and efficiently be made in the form of small multilamellar vesicles. Thus, the invention provides a composition comprising a population of nucleic acid-containing lipid vesicles in a liquid carrier, wherein at least a portion of the lipid vesicles are small:multilamellar vesicles. The small multilamellar vesicles comprise (a) a lipid component comprising 20–30 mol % of an ionizable amino lipid such as DODAP, and a steric barrier lipid such as PEG-CerC$_{14}$; and (b) an oligodeoxynucleotide contained in the lumen or interlamellar spaces of the small multilamellar vesicles. The ODN and lipid components are preferably present in the small multilamellar vesicles in a mole ratio of from 0.15 to 0.25.

The compositions of the invention can be made by a method comprising the steps of:

(a) preparing a lipid mixture comprising 20–30 mol % of an ionizable amino lipid, a steric barrier lipid and additional lipid components selected from among neutral lipids and sterols in an ethanolic solvent;
(b) preparing a solution of oligodeoxynucleotide in an aqueous solvent having a pH at which the ionizable amino lipid is positively charged;
(c) adding the lipid mixture to the solution of oligodeoxynucleotide to form a mixture containing lipid vesicles;

(d) passing the mixture containing lipid vesicles through a filter to produce sized lipid vesicles in a solution containing ethanol;

(e) removing the ethanol from the sized lipid vesicles; and (f) increasing the pH of the solution surrounding the sized lipid vesicles to in reduce the net positive charge on the exterior of the sized lipid vesicles. At least a portion of the A sized lipid vesicles are small multilamellar vesicles.

BRIEF DESCRIPTION OF THE DRAWINGS

FIG. 5 illustrates the quasi-elastic light scattering analysis of encapsulated liposomal antisense. The size distribution of a liposomal preparation of antisense was determined by quasi-elastic light scattering (QELS) immediately after removal of the free antisense (A), and after storage of the preparation for 2 months at 4° C. (B), using a Nicomp Model 370 sub-micron particle sizer.

Figure 11:
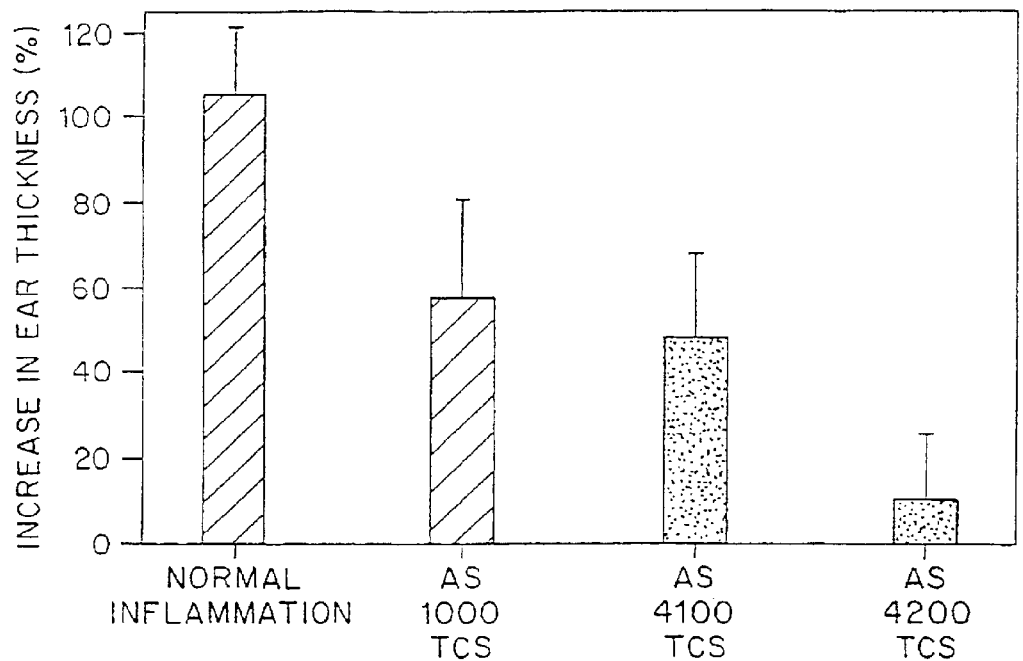

FIG. 11 illustrates the enhanced efficacy of liposomal antisense containing DODAP—ear swelling. Inflamed mice were treated at the time of ear challenge with a 30 mg/kg i.v. dose of either HBS (no oligo), EPC:CHOL liposomes with entrapped PS 3082 (identified as AS 1000), POPC:CHOL:DODAP:PEG-CerC14 with entrapped PS 3082 (identified as 4100), or DSPC:CHOL:DODAP:PEG-CerC14 with entrapped PS 3082 (identified as 4200). Ear swelling was measured at 24 hours after initiating inflammation using an engineer's micrometer.

Figure 12:
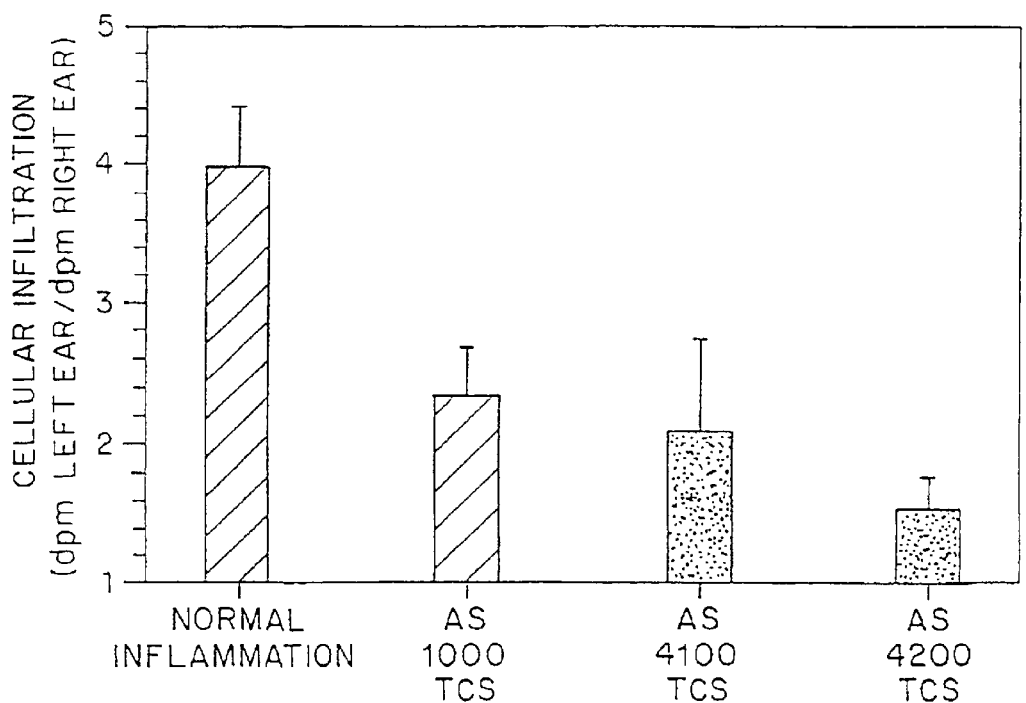

FIG. 12 illustrates the enhanced efficacy of liposomal antisense containing DODAP-cellular infiltration. Mice received 10 μCi of [$^{3}$H]-methylthymidine, i.p., 24 hours before initiating inflammation. Inflamed mice were treated at the time of ear challenge with a 30 mg/kg i.v. dose of either HBS (no oligo), EPC:CHOL liposomes with entrapped PS 3082 (identified as AS 1000), POPC:CHOL:DODAP:PEG-CerC14 with entrapped PS 3082 (identified as 4100), or DSPC:CHOL:DODAP:PEG-CerC14 with entrapped PS 3082 (identified as 4200). Cell infiltration was monitored by measuring the radioactivity in the "challenged ear" versus the non-treated ear. Results are expressed as the ratio of radioactivity in the left (challenged ear) versus right ear.

Figure 13:
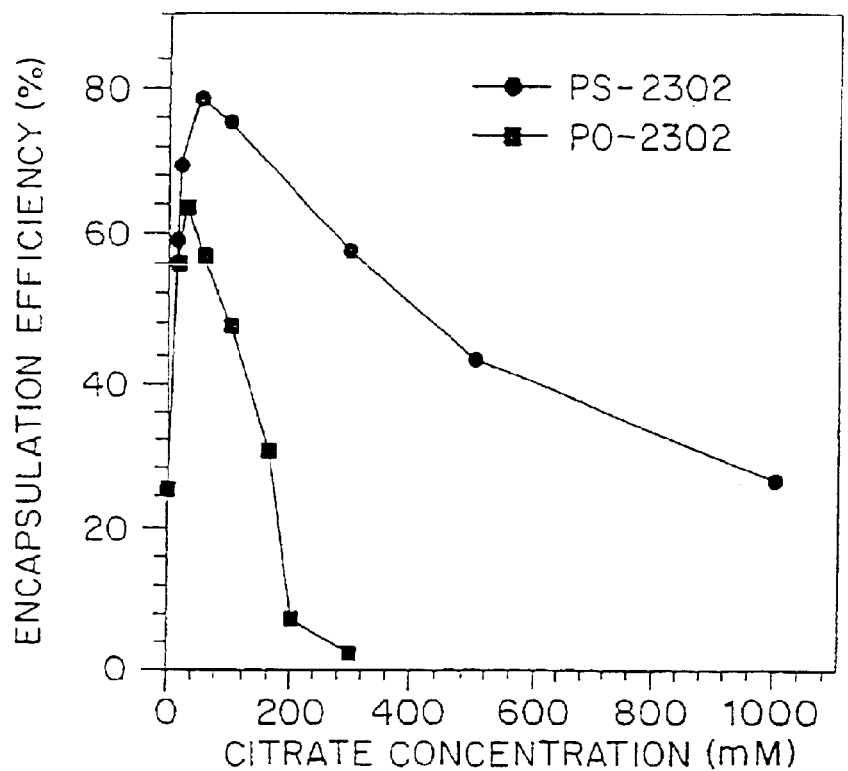

FIG. 13 shows asymmetric loading of lipid-encapsulated-nucleic acid particles in accordance with the invention.

Figure 14:
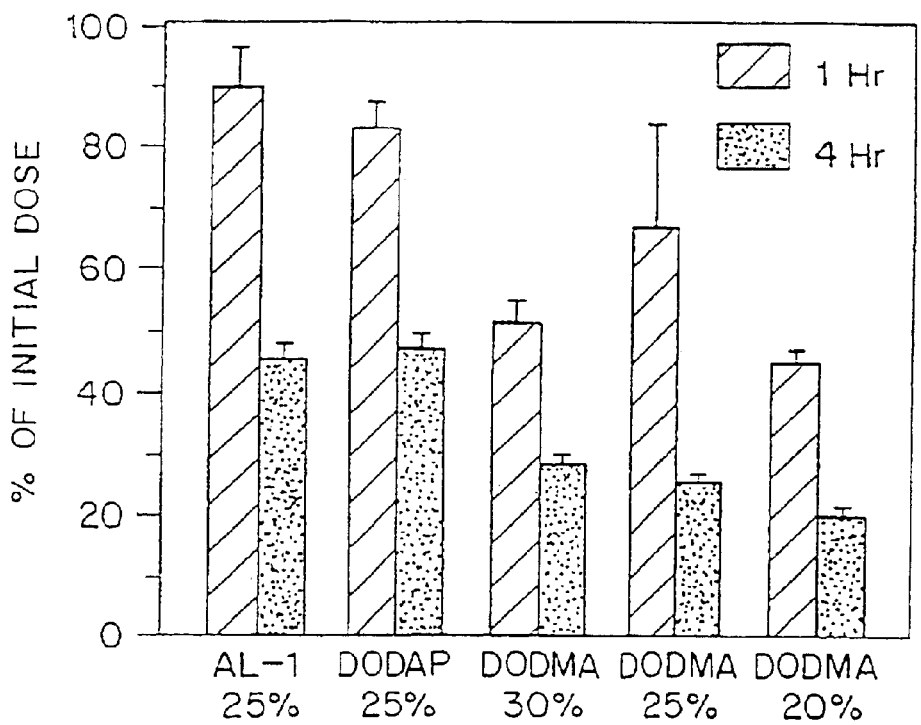

FIG. 14 shows clearance of lipid-encapsulated antisense particles formulated with several amino lipids at different levels.

Figure 15:
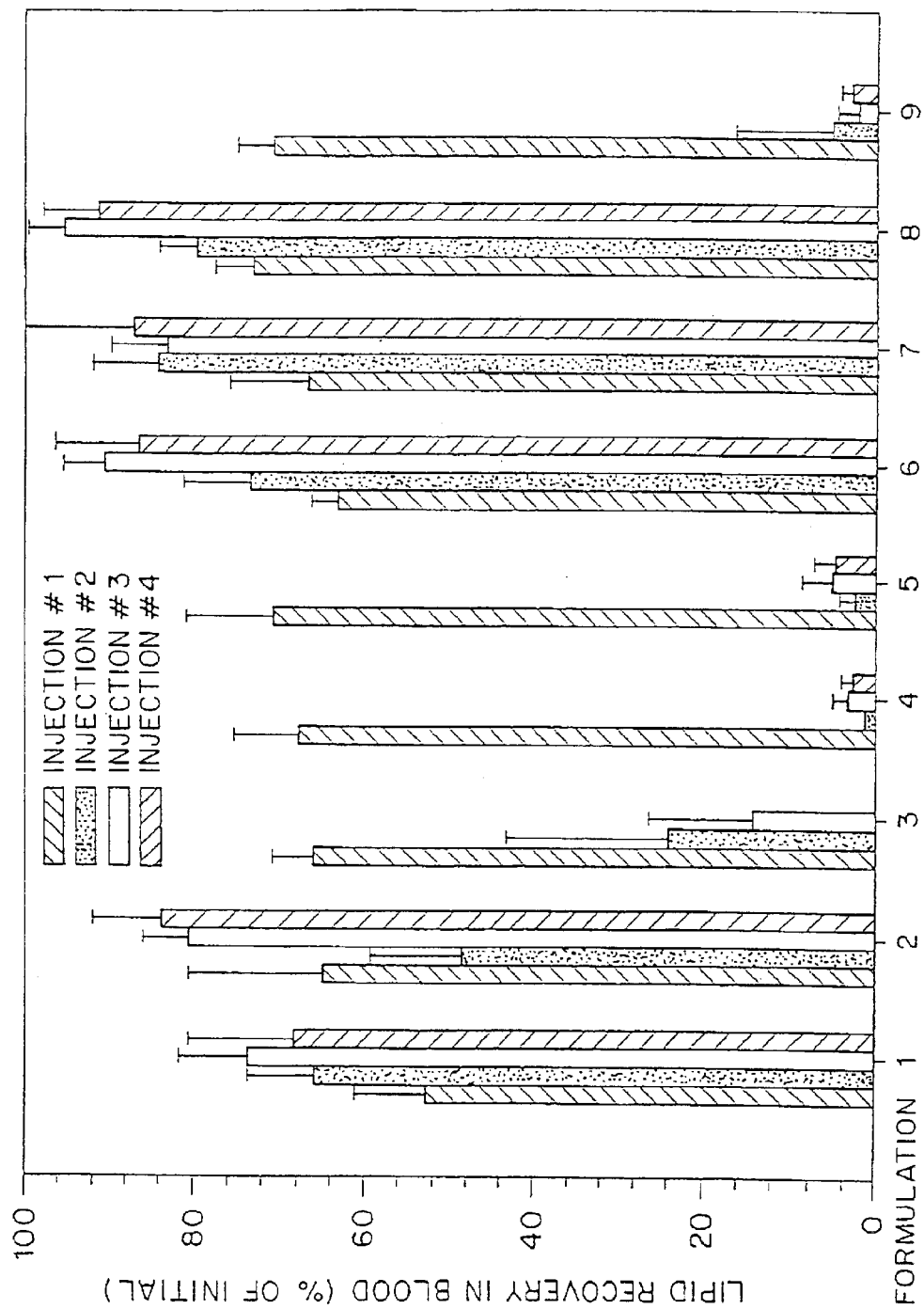

FIG. 15 shows blood levels of antisense-containing particles after repeat dosages.

Figure 16:
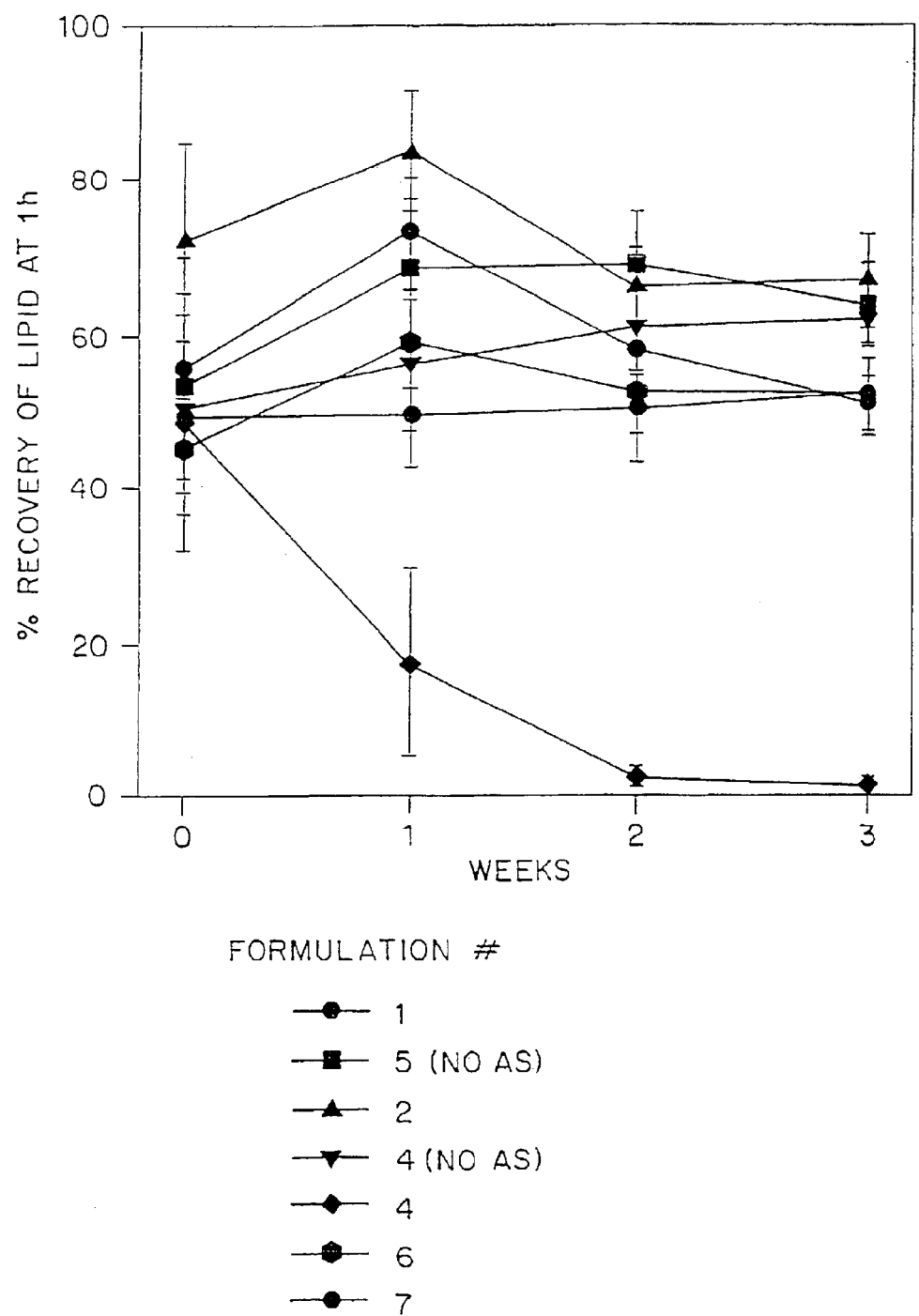

FIG. 16 shows blood levels of antisense-containing particles after repeat dosages.

Figure 17:
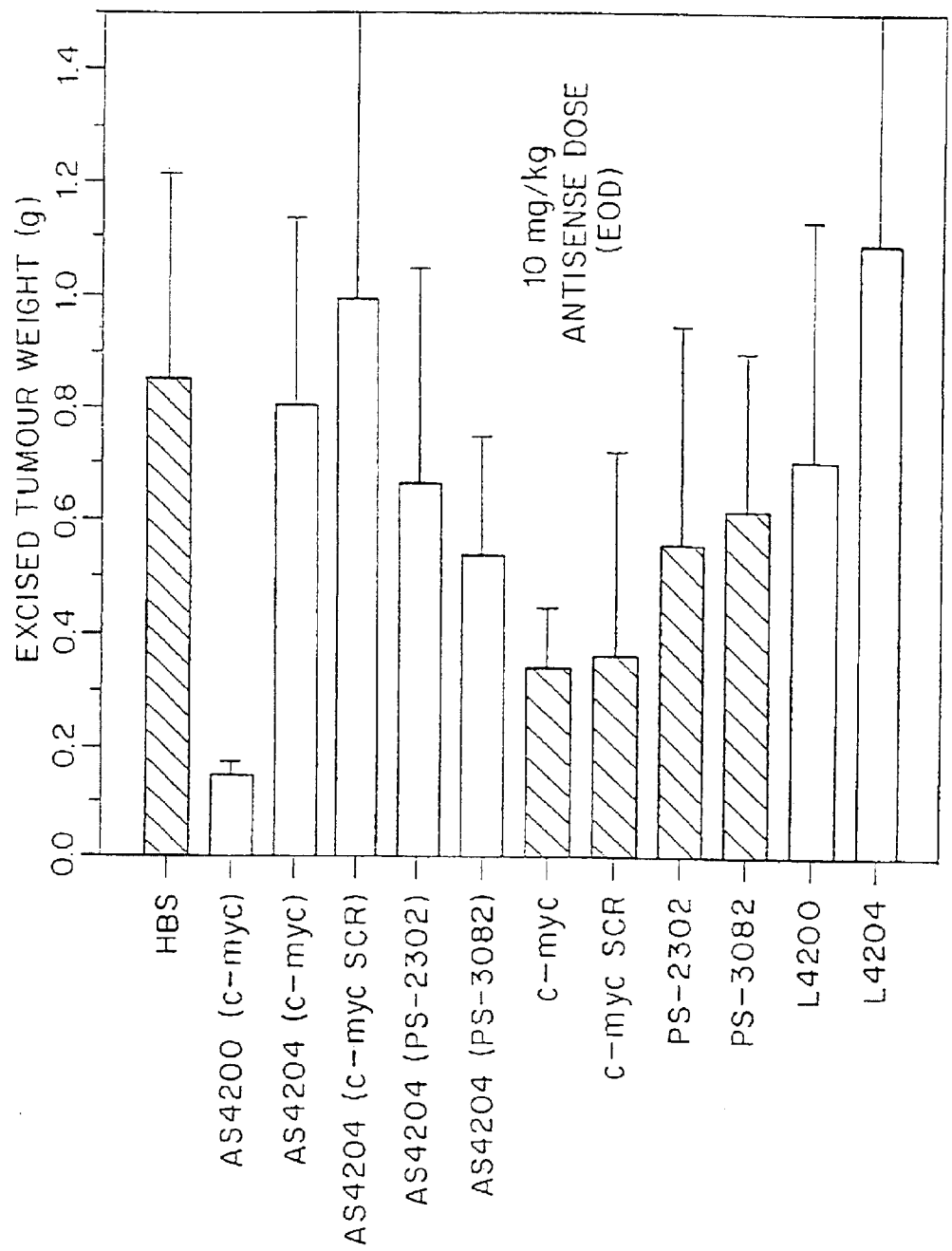

FIG. 17 illustrates results of a study on the in vivo efficacy of lipid-encapsulated antisense particles in accordance with the invention in a mouse tumor model.

Figure 18:
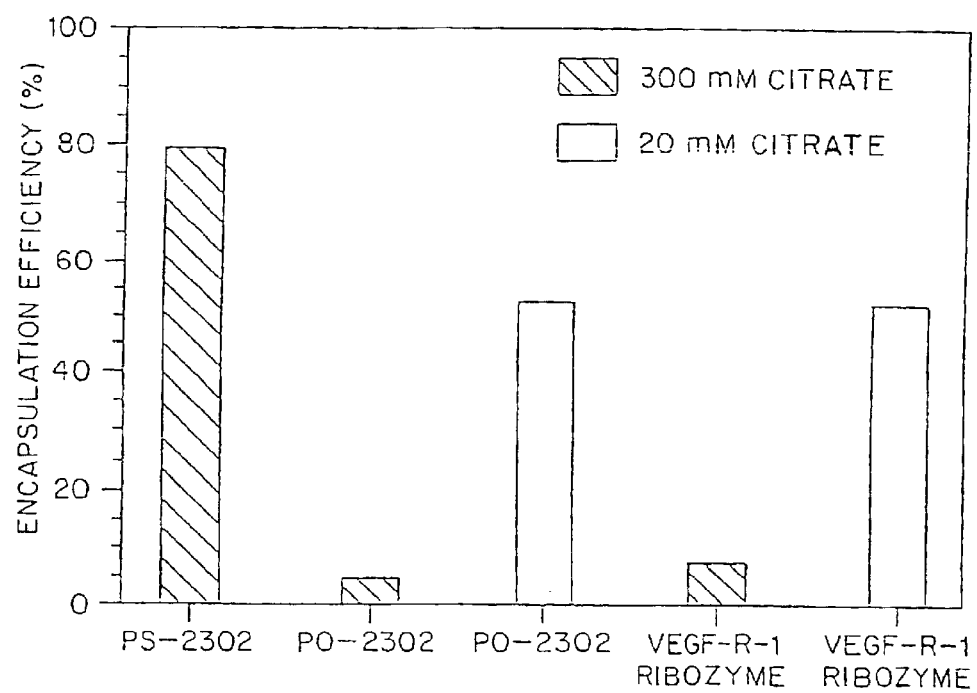

FIG. 18 shows encapsulation efficiency results for lipid-encapsulated therapeutic agent particles in accordance with the invention.

Figure 19:
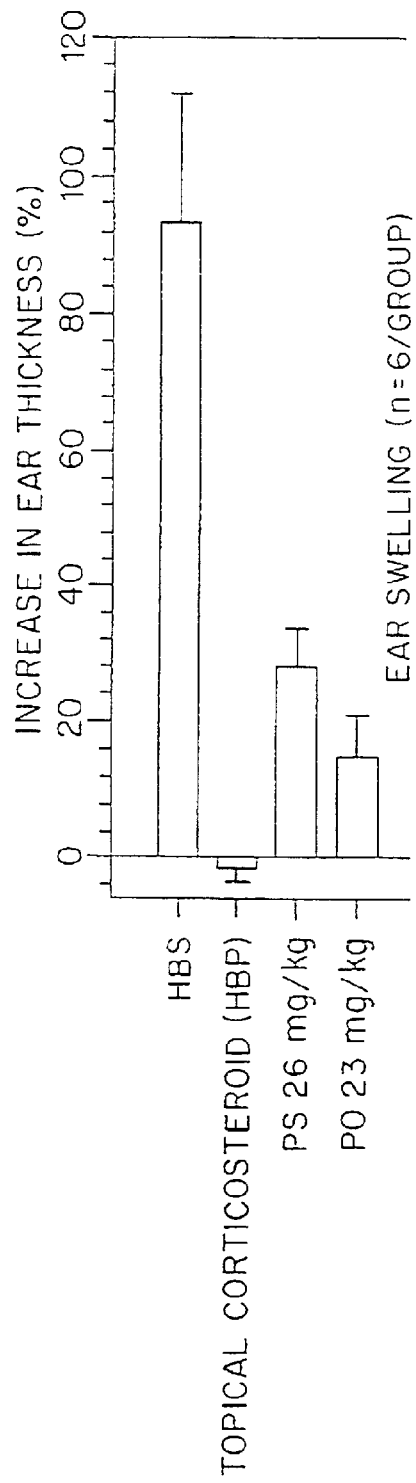

FIG. 19 shows results for studies on the use of murine ICAM1 in an ear inflammation model.

Figure 20:
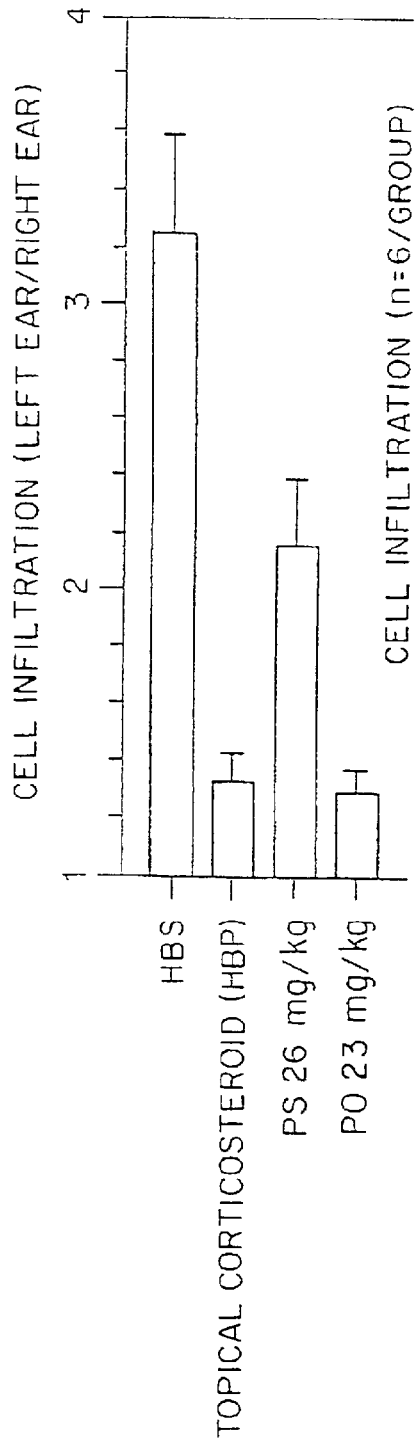

FIG. 20 shows results for studies on the use of murine ICAM1 in an ear inflammation model.

Figure 21:
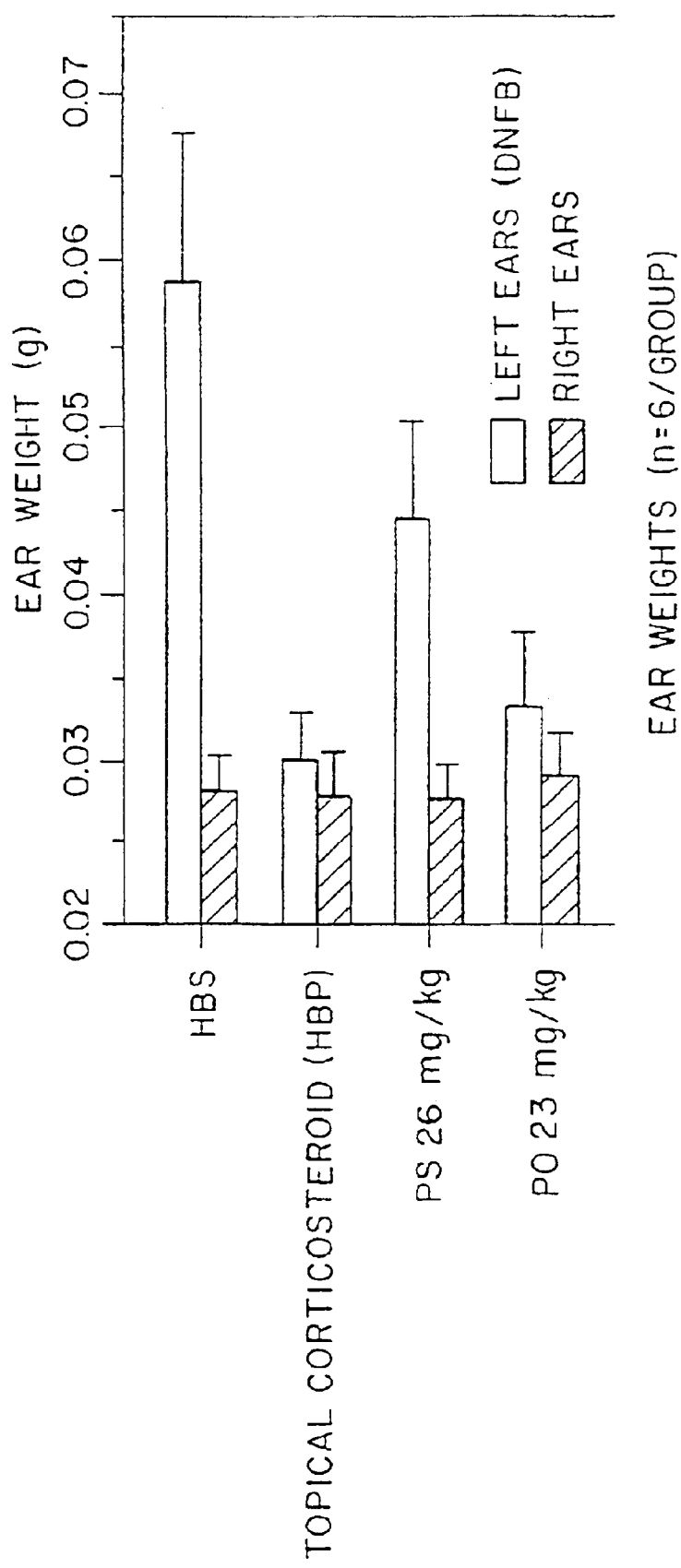

FIG. 21 shows results for studies on the use of murine ICAM1 in an ear inflammation model.

Figure 22:
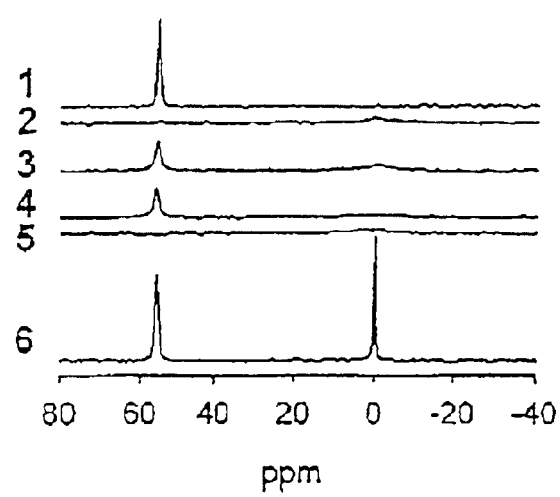

FIG. 22 shows $^{31}$P NMR spectra obtained for encapsulated and unencapsulated c-myc ODN.

DETAILED DESCRIPTION OF THE INVENTION

This application relates to lipidic composition comprising a lipid component and a ODN. As used in the specification and claims of this application, the following definitions and abbreviations are relevant.

Lipid Abbreviations:
Dioleoylphosphatidylethanolamine (DOPE)
Distearoylphosphatidylcholine (DSPC)
Palmitoyloleoylphospahtidylcholine (POPC)
Sphingomyelin (SM)
Egg phosphatidyl choline (EPC)
Dioleoyldimethylammonium chloride (DODAC)
1,2-dioleoyl-3-dimethylammonium propane (DODAP)
in N-(1-(2,3-dioleoyloxy)propyl)-N,N-dimethyl ammonium chloride, and its protonated ammonium form (DODMA)
Cholesterol (CHOL)
Cholesterylhexadecylether (CHE)
1-O-(2'-(ω-methoxypolyethylene glycol)succinyl)-2-N-myristylshingosine (PEG-CerC$_{14}$)
1-O-(2'-(ω-methoxypolyethylene glycol)succinyl)-2-N-arachidoylshingosine (PEG-CerC$_{2}$)

"Therapeutically effective amount" means an amount which provides a therapeutic benefit. For antisense oligonucleotide this means generally 0.5 to 50 mg/kg of body weight, but when delivered in a lipid particle formulation, a below-toxic amount of lipid must be used.

"Lipid exchange out of particle" and the rate of this exchange is fully explained in U.S. patent application Ser. Nos. 08/486,214 and 08/485,608 and PCT Patent publications WO 96/10391 and WO 96/10392, which are all incorporated herein by reference. Lipid exchange into the surrounding medium is possible for lipids which are reversibly associated with the lipid particle membrane. Each lipid has a characteristic rate at which it will exchange put of a particle which depends on a variety of factors including acyl chain length, saturation, head group size, buffer composition and membrane composition.

"Disease site" is the site in an organism which demonstrates or is the source of a pathology. The disease site may be focused, as in a site of neoplasm or inflammation, or may be diffuse as in the case of a non-solid tumor. "Administration at a site which is distal to the disease site" means that delivery to the disease site will require some kind of systemic delivery, either by blood or lymph circulation, or other fluid movement inside the organism.

The term "oligodeoxynucleotide" or "ODN" refers to relatively short, single stranded nucleic acid polymers, i.e, to polymers having a length of less than about 50 bases.

The compositions of the invention comprise a population of ODN-containing lipid vesicles in an aqueous carrier, wherein at least a portion of the lipid vesicles are small multilamellar vesicles (SMV). After formation and extrusion, the SMV have an average diameter of about 100 nm. Typically, the SMV have from 6 to 9 lamellae arranged as concentric rings, with the innermost lamellae having a diameter of as small as 20 nm. Freeze fracture electron microscopy and quasi-elastic light scattering (QELS) reveal that the membrane structures of each SMV are closely associated, however many SMV share a common feature where the outer 2–4 lamellae at one side of the particle appear to separate.

The SMV are formed from a lipid component and a ODN. The lipid component comprises 20–30 mol %, and more preferably 20–25% of an ionizable amino lipid. The ionizable lipid is selected such that raising the pH surrounding the small multilamellar vesicles to a pH of around 7.5 results in the release of external, non-encapsulated oligodeoxynucleotides A preferred ionizable amino lipid is DODAP. Other ionizable lipids which could be used include DODMA.

The lipid component of the compositions of the invention also comprises a steric barrier lipid. Suitable steric barrier lipids include PEG-lipids such as PEG-CerC$_{14}$ and PEG- CerC$_{20}$. Other examples of steric barrier lipids which can be used include polyamide oligomer lipids (PAO-lipids) and gangliosides. The steric barrier lipid is typically incorporated at a level of about 10 mol %.

The balance of the lipid component of the SMV comprises additional lipids selected from among neutral lipids (such as DOPE, DSPC, POPC and, SM) and sterols (such as CHOL). Thus, a preferred lipid composition from use as the lipid component in the compositions of the invention contains DSPC, CHOL, DODAP and PEG-$CerC_{14}$ in a molar ratio of 25:45:20:10.

The composition of the invention also comprises an ODN contained in the lumen or interlamellar spaces of the SMV. The ODN is selected based upon the therapeutic effect desired, and the size and characteristics of the ODN are not critical. Suitable ODN are antisense species having a length of 15–24 bases. The ODN may be one which contains exclusively phosphodiester internucleotide linkages, or it may include modified linkages such as phosphorothioate linkages.

Particular, non-limiting examples of ODNs which can be used in the compositions of the invention are antisense ODN having the following sequences and mRNA targets:

| Trivial Name: | Gene Target, Chemistry and Sequence | |
|---|---|---|
| PS-3082 | murine ICAM-1 (Intracellular Adhesion Molecule-1) (phosphorothioate) TGCATCCCCCAGGCCACCAT | (SEQ ID. No 1) |
| PO-3082 | murine ICAM-1 (phosphodiester) TGCATCCCCCAGGCCACCAT | (SEQ ID. No 1) |
| PS-2302 | human ICAM-1 (phosphorothioate) GCCCAAGCTGGCATCCGTCA | (SEQ ID. No 2) |
| PO-2302 | human ICAM-1 (phosphodiester) GCCCAAGCTGGCATCCGTCA | (SEQ ID. No 2) |
| PS-8997 | human ICAM-1 (phosphorothioate) GCCCAAGCTGGCATCCGTCA | (SEQ ID. No 2) |
| PO-8997 | human ICAM-1 (phosphodiester) GCCCAAGCTGGCATCCGTCA | (SEQ ID. No 2) |
| US3 | human erb-B-2 gene (phosphodiester or phosphorothioate) GGT GCT CAC TGC GGC | (SEQ ID. No 3) |
| LR-3280 | human c-myc gene (phosphorothioate) AAC GTT GAG GGG CAT | (SEQ ID. No 4) |
| Inx-6298 | human c-myc gene (phosphodiester) AAC GTT GAG GGG CAT | (SEQ ID. No 4) |
| Inx-6295 | human c-myc gene (phosphodiester or phosphorothioate) T AAC GTT GAG GGG CAT | (SEQ ID. No 5) |
| LR-3001 | human c-myb gene (phosphodiester or phosphorothioate) TAT GCT GTG CCG GGG TCT TCG GGC | (SEQ ID. No 6) |
| c-myb | human c-myb gene (phosphodiester or phosphorothioate) GTG CCG GGG TCT TCG GGC | (SEQ ID. No 7) |
| IGF-1R | human IGF-1R (Insulin Growth Factor 1 - Receptor) (phosphodiester or phosphorothioate) GGA CCC TCC TCC GGA GCC | (SEQ ID. No 8) |
| LR-42 | human IGF-1R (phosphodiester or phosphorothioate) TCC TCC GGA GCC AGA CTT | (SEQ ID. No 9) |
| EGFR | human EGFR (Epidermal Growth Factor Receptor) (phosphodiester or phosphorothioate) CCG TGG TCA TGC TCC | (SEQ ID. No 10) |
| VEGF | human VEGF (Vascular Endothelial Growth Factor) gene (phosphodiester or phosphorothioate) CAG CCT GGC TCA CCG CCT TGG | (SEQ ID. No 11) |
| PS-4189 | murine PKC-alpha (Phosphokinase C - alpha) gene (phosphodiester or phosphorothioate) CAG CCA TGG TTC CCC CCA AC | (SEQ ID. No 12) |
| PS-3521 | human PKC-alpha (phosphodiester or phosphorothioate) GTT CTC GCT GGT GAG TTT CA | (SEQ ID. No 13) |
| Bcl-2 | human bcl-2 gene (phosphodiester or phosphorothioate) TCT CCC AgC gTg CgC CAT | (SEQ ID. No 14) |
| ATG-AS | human c-raf-1 protein kinase (phosphodiester or phosphorothioate) GTG CTC CAT TGA TGC | (SEQ ID. No 15) |
| VEGF-R1 | human VEGF-R-1 (Vascular Endothelial Growth Factor Receptor 1) ribozyme GAG UUG CUG AUG AGG CCG AAA GGC CGA AAG UCU G | (SEQ ID. No 16) |

Alternatively, oligonucleotides which do not hybridize to the human genome may be used. Such sequences are particularly desired if they contain immune-stimulating sequences (ISS) of nucleotides, such as CpG and palindromic sequences. Certain oligonucleotides are inherently immune stimulating in the free form; others can be made to be immune stimulating by encapsulation in the lipid particle.

Using these sequences, the invention provides a method for the treatment of a diseases, including tumors, characterized by aberrant expression of a gene in a mammalian subject. The method comprises the steps of preparing a lipid-encapsulated therapeutic nucleic acid particle according to the methods as described herein, where the therapeutic nucleic acid component hybridizes specifically with the aberrantly expressed gene; and administering a therapeutically effective amount of the resulting particle to the mammalian subject. These sequences are, of course, only representative of the possible therapeutic oligonucleotide compounds that can be delivered using the invention. It is well known that, depending on the target gene, antisense that hybridizes to any part of the target gene, such as coding regions, introns, the 5' untranslated region (5'UTR), start of translation, or 3'UTR may have therapeutic utility. Therefore, the sequences listed above are only exemplary of antisense. In short, the compounds listed above represent the broad class of therapeutic 5–50 mer oligonucleotides of various chemistries which are useful with this invention. Other ODN which are useful include all those which have previously demonstrated efficacy in the free form.

Additionally, the nucleic acid can carry a label (e.g., radioactive label, fluorescent label or colorimetric label) for the purpose of providing clinical diagnosis relating to the presence or absence of complementary nucleic acids. Accordingly, the nucleic acids, or nucleotide polymers, can be polymers of nucleic acids including genomic DNA, cDNA, mRNA or oligonucleotides containing nucleic acid analogs, for example, the antisense derivatives described in a review by Stein, et al., Science 261:1004–1011 (1993) and in U.S. Pat. Nos. 5,264,423 and 5,276,019, the disclosures of which are incorporated herein by reference.

The extent to which SMV's are present in the compositions of the invention depends on the ODN-to-lipid ratio. When compositions with a low ODN-to-lipid ratio (0.025 w/w) were evaluated by cryo-electron microscopy, 7 of 18 of the structures observed were partial SMVs. On the other hand, when a high ODN-to-lipid ratio (0.25 w/w) was used, 6 of 7 structures were SMVs. Intermediate ODN-to-lipid ratios would be expected to provide intermediate results. Thus, for obtaining compositions with substantial numbers of SMVs, the ODN and lipid component are present in the small multilamellar vesicles in a weight ratio of from 0.15 to 0.25, preferably 0.15 to 0.20. As described below, this nucleic acid:lipid ratio is readily achieved in the method of the invention by controlling the starting nucleic acid:lipid ratio and the concentration of ethanol in the combined solutions.

Increasing the ODN-to-lipid ratio also results in an increase in the number of layers per particle. This has important consequences when one is selecting the appropriate ODN-to-lipid ratio for a particular application. For example, high ODN-to-lipid ratio particles are preferred for vaccine compositions. Uptake into the immune system cells, and the onion skin effect (where layers of ODN are released successively) will prolong and reinforce immune stimulation effects. Low ODN-to-lipid ratio particles are preferred for "payload delivery" applications, because the payload is released all at once.

Finally, the ODN-to-lipid ratio may have a bearing on the appropriate dosage to used in therapeutic applications. It has been observed that below about 50 mg/kg lipid, liposomes are rapidly removed from circulation by the RES. A higher dose is required to have sustainable liposome circulation. Generally this means that a standard liposomal dose is about 100 mg/kg. In the case of a high ODN-to-lipid ratio, however, the effective lipid dose will be less. Thus, in this circumstance, a higher dosage may be required for sustainable liposomal circulation.

SMV in the compositions of the invention are formed by mixing a lipid solution with a solution containing the ODN and extruding the resulting particles. The lipid solution contains all of the lipid components discussed above in an ethanolic solvent. The solvent may be an aqueous ethanol solvent, or it may preferably be 100% ethanol. The solvent for the solution of ODNs is an aqueous solvent, for example 300 mM citrate buffer, pH 4.0, and it may optionally contain ethanol. The ethanol levels in the two solvents are selected such that the lipids and the ODNs are soluble in their respective solvents, and such that when the appropriate amounts of the lipid solution and the solution containing the ODNs are combined the final ethanol concentration will be in the range of 20 to 40% to achieve encapsulation efficiencies of greater than 50%, preferably in the range of 30 to 40%.

The appropriate amounts of lipid solution and the solution containing the ODN is determined from the starting concentrations of lipids, the starting concentration of ODNs and the desired ratio of lipids to ODNs. Thus, for example, if the ethanol level is selected to achieve 65% encapsulation (about 30% ethanol), and the desired ration of ODN to lipid is 0.2 (w/w), then the total weight of lipid needs to be about 3.25 times the total weight of ODN (0.65/0.2).

The lipid solution is slowly added to the solution containing ODNs, suitably after warming to a temperature of 65° C. for 2–3 minutes, with constant mixing. The resulting mixture is extruded and then dialyzed to remove excess ethanol. It is then further dialyzed against a buffer to remove citrate buffer, neutralize the positive surface charges of the ionizable amino lipid and release any ODN that may be associated with the surface of the vesicle. This released nucleic polymer may be removed by column chromatography to yield a preparation suitable for therapeutic use.

While the foregoing provides an overview of the invention, the methods and compositions will now be further described with reference to the following, non-limiting examples.

Materials and Methods

Materials and Methods:

Lipids

Distearoylphosphatidylcholine (DSPC), sphingomyelin (SM), and palmitoyloleoylphosphatidylcholine (POPC) were purchased from Northern Lipids (Vancouver, Canada). 1,2-dioleoyloxy-3-dimethylammoniumpropane (DODAP or AL-1) was synthesized by Dr. Steven Ansell (Inex Pharmaceuticals) or, alternatively, was purchased from Avanti Polar Lipids. Cholesterol was purchased from Sigma Chemical Company (St. Louis, Mo., USA). PEG-ceramides were synthesized by Dr. Zhao Wang at Inex Pharmaceuticals Corp. using procedures described in PCT WO 96/40964, incorporated herein by reference. [$^3$H] or [$^{14}$C]-CHE was purchased from NEN (Boston, Mass., USA). All lipids were >99% pure.

Buffers and Solvents

Ethanol (95%), methanol, chloroform, citric acid, HEPES and NaCl were all purchased from commercial suppliers.

Synthesis and Purification of Phosphorothioate Antisense

PS 3082, a 20mer phosphorothioate antisense oligodeoxynucleotide, was synthesized, purified and donated by ISIS Pharmaceuticals (Carlsbad, Calif., USA). The sequence for this oligo is: TGCATCCCCCAGGCCAC-CAT. (Seq ID No 1) The details of the synthesis and purification can be found elsewhere (see, Stepkowski, et al., *J. Immunol.* 153:5336–5346 (1994)).

Preparation of Liposomal Antisense

Lipid stock solutions were prepared in 95% ethanol at 20 mg/mL (PEG-Ceramides were prepared at 50 mg/mL). DSPC, CHOL, DODAP, PEG-CerC14 (25:45:20:10, molar ratio), 13 µmol total lipid, were added to a 13×100 mm test tube containing trace amounts of [$^{14}$C]-cholesterylhexadecylether. Note that the CHE is added as a label and is not required for the structure of the SMV. The final volume of the lipid mixture was 0.4 mL. In some experiments, SM or POPC was substituted for DSPC. A 20mer antisense oligodeoxynucleotide, PS 3082 (2 mg), and trace amounts of [$^3$H]-PS 3082 were dissolved in 0.6 mL of 300 mM citric acid, pH 3.8 in a separate 13×100 mm test tube. The antisense solution was warmed to 65° C. and the lipids (in ethanol) were slowly added, mixing constantly. The resulting volume of the mixture was 1.0 mL and contained 13 µmol total lipid, 2 mg of antisense oligodeoxynucleotide, and 38% ethanol, vol/vol. The antisense-lipid mixture was subjected to 5 cycles of freezing (liquid nitrogen) and thawing (65° C.), and subsequently was passed 10×through three stacked 100 nm filters (Poretics) using a pressurized extruder apparatus with a thermobarrel attachment (Lipex Biomembranes). The temperature and pressure during extrusion were 65° C. and 300–400 psi (nitrogen), respectively. The extruded preparation was diluted with 1.0 mL of 300 mM citric acid, pH 3.8, reducing the ethanol content to 20%. The preparation was immediately applied to a gel filtration column. Alternatively, the extruded sample was dialyzed (12 000–14 000 MW cutoff; SpectraPor) against several liters of 300 mM citrate buffer, pH 3.8 for 34 hours to remove the excess ethanol. The sample was subsequently dialyzed against HBS, pH 7.5, for 12–18 hours to neutralize the DODAP and release any antisense that was associated with the surface of the vesicles. The free antisense was removed from the encapsulated liposomal antisense by gel exclusion chromatography as described below.

Gel Filtration Chromatography

A 20×2.5 cm glass column containing Biogel A15m, 100–200 mesh, was equilibrated in HEPES-buffered saline (HBS; 20 mM HEPES, 145 mM NaCl, pH 7.5). The 2.0 mL liposomal antisense preparation was applied to the column and allowed to drain into the gel bed under gravity. The column was eluted with HBS at a flow rate of 50 mL/hr. Column fractions (1.0 mL) were collected and analyzed for radioactivity using standard liquid scintillation counting techniques. The fractions were pooled based on the levels of [$^{14}$C]-CHE present in the fraction. The size distribution of the pooled liposomal antisense was determined using a NICOMP Model 370 Sub-micron particle sizer and was typically 110×35 nm.

Ion Exchange Chromatography

As an alternative to gel filtration chromatography, samples were sometimes dialyzed first in 300 mM citrate, pH 3.80, for 2–3 hours to remove residual ethanol, followed by at least a 12 hour dialysis in HBS, to exchange the external citrate for HBS and remove residual ethanol. The sample was applied to a 1.5×8 cm DEAE-Sepharose® column equilibrated in HBS. Free oligonucleotide binds to the DEAE with very high affinity. The peak containing the lipid was pooled, concentrated, and analyzed for antisense content, as described below.

Assessment of Antisense Encapsulation

Antisense encapsulation was typically assessed by dual label ([$^3$H]-antisense and [$^{14}$C)-lipid) liquid scintillation counting after gel filtration chromatography to separate the free and encapsulated antisense. Antisense encapsulation was evaluated by summing the total [$^3$H]-antisense radioactivity associated with the lipid peak and dividing by the total [$^3$H]-antisense radioactivity. Alternatively, the [$^3$H]/[$^{14}$C] ratio was determined before and after (i.e., in the pooled lipid peak) gel filtration chromatography. Antisense encapsulation was also assessed by measuring the absorbance of the sample at 260 nm, preceded by a Bligh and Dyer extraction of the antisense from the lipid, as described below.

Extraction of the Antisense

The antisense was extracted from the lipid according to the procedure outlined by Bligh and Dyer (Bligh, et al., Can. *J. Biochem. Physiol.* 37:911–917 (1959)). Briefly, up to 250 FL of aqueous sample was added to a 13×100 mm glass test tube, followed by the addition of 750 µL of chloroform-:methanol (1:2.1, vol/vol), 250 µL of chloroform, and 250 µL of distilled water. The sample was mixed after each addition. The sample was centrifuged for 10 min. at 3000 rpm, resulting in a clear two-phase separation. The aqueous phase (top) was removed into a new 13×100 mm test tube. An aliquot (500 µL) of this phase was diluted with 500 µL of distilled water, mixed, and the absorbance at 260 nm was assessed using a spectrophotometer. In some instances, the organic phase (bottom) was washed with 250 µL of methanol, centrifuged for 10 min. at 3000 rpm, and the upper phase removed and discarded. This was repeated 3 times. The washed organic phase was assessed for phospholipid content according to the method of Fiske and Subbarrow (Fiske, et al., *J. Biol. Chem.* 66:375400 (1925)).

OLIGREEN Assay

A fluorescent dye binding assay for quantifying single stranded oligonucleotide in aqueous solutions was established using a Biolumin™ 960 fluorescent plate reader (Molecular Dynamics, Sunnyvale, Calif., USA). Briefly, aliquots of encapsulated oligonucleotide were diluted in HEPES buffered saline (HBS; 20 mM HEPES, 145 mM NaCl, pH 7.5). A 10 µL aliquot of the diluted sample was added to 100 µL of a 1:200 dilution of Oligreen™ reagent, both with and without 0.1% of Triton X-100 detergent. An oligo standard curve was prepared with and without 0.1% Triton X-100 for quantification of encapsulated oligo. Fluorescence of the OLIGREEN™-antisense complex was measured using excitation and emission wavelengths of 485 nm and 520 mm, respectively. Surface associated antisense was determined by comparing the fluorescence measurements in the absence and presence of detergent.

$^{31}$P NMR Spectroscopy $^{31}$P NMR spectra were obtained using a Brucker MSL200 spectrometer operating at 81 MHz. Free induction decays (FIDs) corresponding to 800 scans were obtained by using a 2.8 µs pulse with a 3 s interpulse delay and a spectral width of 20,000 Hz on a 200 ml sample in a 10 mm probe. No proton decoupling was used. An exponential multiplication corresponding to 25 Hz of line broadening was applied to the FIDs prior to Fourier transformation. The chemical shift was referenced to external phosphoric acid ($H_3PO_4$). In some instances, ammonium acetate (150 mM) was added to the exterior of the lipid particles and the pH adjusted to 7.4 with NaOH. Ammonium acetate equilibrates the interior and exterior pH of lipid vesicles. In designated spectra, 5 mM MnSO$_4$ was added to the exterior of the vesicles as a membrane impermeable paramagnetic line-broadening agent that quenches the signals of all accessible phosphate groups, including phospholipids and ODN.

Cryo-Electron Microscopy

A single drop of the SMV compositions was applied to a standard electron microscope grid with a perforated carbon film. Excess liquid was removed by blotting, leaving a thin layer of the suspension covering the holes of the carbon fil, The grid was rapidly frozen in liquid ethane, resulting in vesicles embedded in a thin film of amorphous ice. Images of the vesicles in the ice were obtained under cryogenic conditions at a magnification of 50,000 and a defocus of −1.5 microns using a Gatan cryo-holder in a Phillips CM200 FEG electron microscope.

Ear Inflammation Model and Efficacy Studies

Sensitization and Elicitation of Contact Sensitivity

Mice were sensitized by applying 25 μL of 0.5% 2,4-dinitro-1-fluorobenzene (DNFB) in acetone:olive oil (4:1) to the shaved abdominal wall for two consecutive days. Four days after the second application, mice were challenged on the dorsal surface of the left ear with 10 μL of 0.2% DNFB in acetone:olive oil (4:1). Mice received no treatment on the contralateral (right) ear. In some cases, control mice received 10 μL of vehicle on the dorsal surface of the left ear.

Evaluation of Ear Swelling

Ear thickness was measured immediately prior to ear challenge, and at various time intervals after DNFB challenge, using an engineer's micrometer (Mitutoyo, Tokyo, Japan). Increases in ear thickness measurements were determined by subtracting the pre-challenge from post-challenge measurements.

Figure 10:
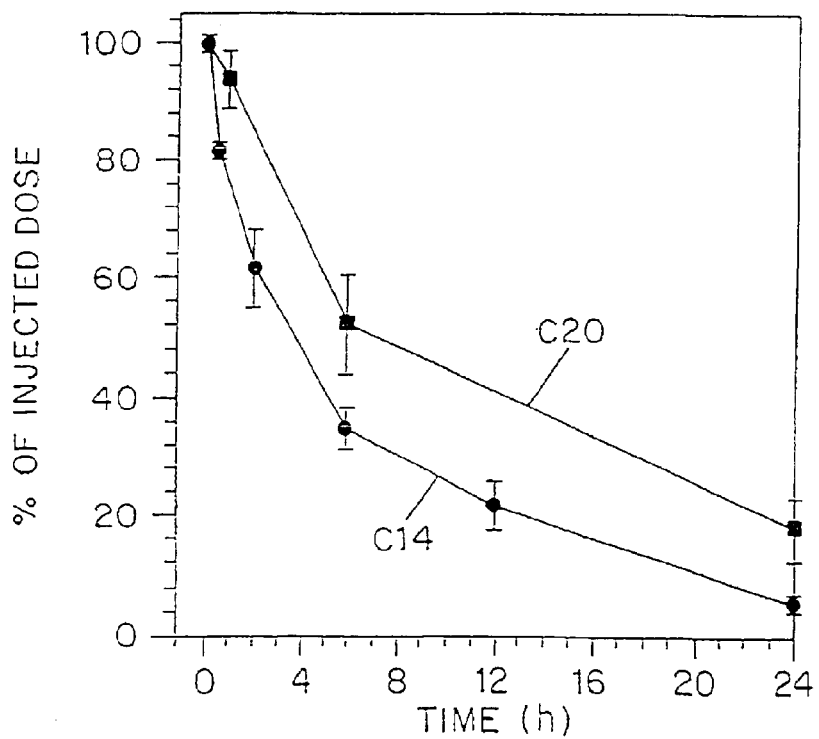
FIG. 10 illustrates the influence of PEG-acyl chain lengths on plasma clearance of encapsulated antisense. Encapsulated liposomal antisense was prepared using the ethanol-citrate procedure as described in "Material and Methods". Initial lipid and antisense concentrations were 9.9 and 2 mg/mL, respectively. Liposomal formulations were composed of DSPC:CHOL:DODAP:PEG-CerC14 or C20 (25:45:20:10). The formulation contained a lipid label ([$^{14}$C]-cholesterylhexadecylether) and [$^{3}$H]-antisense and were injected (200 μL) C) intravenously via the lateral tail vein of female (20–25 g) ICR mice at a lipid dose of 120 mg/kg. Blood was recovered by cardiac puncture on anesthetized mice. Lipid and antisense recoveries were determined by standard scintillation counting techniques.

The progression of ear inflammation over a 3 day period for ICR (outbred) mice is indicated in FIGS. 10 and 11. Erythema was evident almost immediately after ear challenge and gradually declined in intensity over the remainder of the study. ICR mice exhibited peak ear thickness at 24 hours after the induction of ear inflammation. Maximal ear thickness measurements were found to be 170×104 inches, corresponding to a 70% increase in ear thickness. Although ear swelling gradually declines at 48 and 72 hours after inflammation initiation, ear measurements still have not returned to baseline thickness levels (90–100×10$^{-4}$ inches).

The mouse in vivo experimental systems in this specification were selected in part because of their high degree of correlation to human disease conditions. The mouse ear inflammation model, which can be treated using methods and compositions of the invention, is well known to be an excellent model for human allergic contact dermatitis and other disease conditions. The control therapeutic used in this model is a corticosteroid which demonstrates efficacy both in the mouse model and in related human disease conditions.

The mouse B16 tumor model, a fast growing melanoma, which can be treated using methods and compositions of the invention, is a standard, widely used experimental system. This tumor model can be successfully treated using vinca alkaloids, such as vincristine or vinblastine, which are known to be efficacious against human tumors as well.

Treatments which demonstrate utility in the mouse models of this invention are excellent candidates for testing against human disease conditions, at similar dosages and administration modalities.

EXAMPLE 1

This example illustrates the effects of ethanol on the encapsulation of antisense.

A 20mer of [$^3$H]-phosphorothioate antisense oligodeoxynucleotide (in 300 mM citrate buffer, pH 3.80) was mixed with an ethanol solution of lipid (DSPC:CHOL:DODAP:PEG-CerC14; 25:45:20:10, molar ratio) at final concentrations of 2 mg/mL and 9.9 mg/mL, respectively. The final ethanol concentration in the preparations was varied between 0 and 60%, vol/vol. The samples were extruded ten times through three 100 nm filters as described in "Materials and Methods". The samples were dialyzed for 2–3 hours in 300 mM citrate buffer, pH 3.80, to remove a majority of the excess ethanol. The samples were switched to HEPES-buffered saline (HBS), pH 7.50, and dialyzed for a minimum of 12 hours to replace the external citrate buffer with HBS. This renders the majority of DODAP in the outer bilayer neutral, and will release any surface bound antisense. Non-encapsulated antisense was then removed from the liposomal antisense by DEAE-sepharose chromatography as described in "Material and Methods". Encapsulation was assessed either by analyzing the pre-column and post-column ratios of [$^3$H]-antisense and [$^{14}$C]-lipid or by determining the total pre-column and post-column [$^3$H]-antisense and [$^{14}$C]-lipid radioactivity.

In another experiment, the formulations were prepared as described. After extrusion, the filters were analyzed for [$^3$H]-antisense and [$^{14}$C]-lipid radioactivity by standard scintillation counting techniques. Results were expressed as a percent of the total initial radioactivity.

Figure 1:
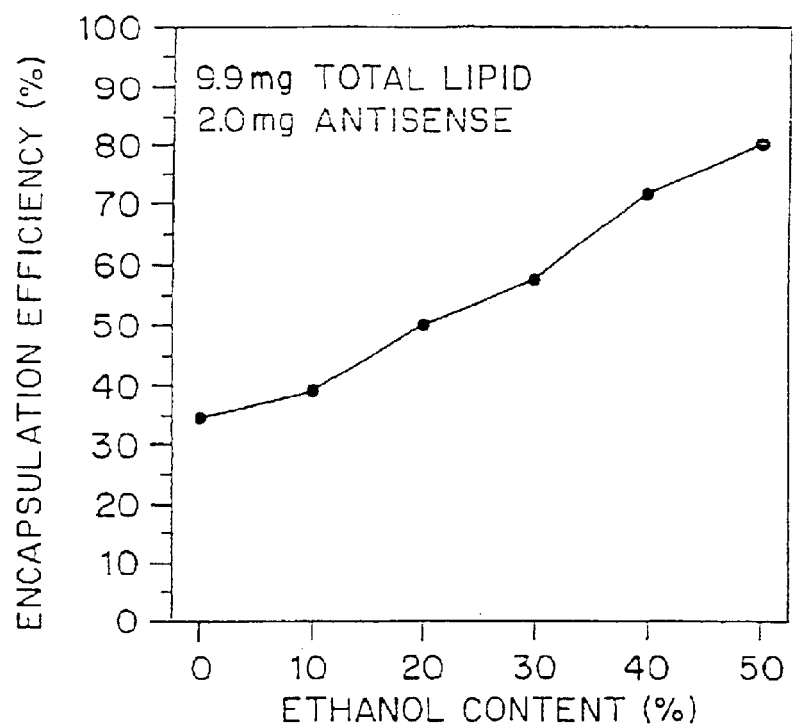
FIG. 1 illustrates the influence of ethanol on the encapsulation of antisense oligodeoxynucleotides. The liposomal antisense compositions were prepared as described in the Examples, with the final concentrations of antisense and lipids being 2 mg/mL and 9.9 mg/mL, respectively. The final ethanol concentration in the preparations was varied between 0 and 60%, vol/vol. Encapsulation was assessed either by analyzing the pre-column and post-column ratios of [$^3$H]-antisense and [$^{14}$C]-lipid or by determining the total pre-column and post-column [$^3$H]-antisense and [$^{14}$C]-lipid radioactivity.
Figure 2:
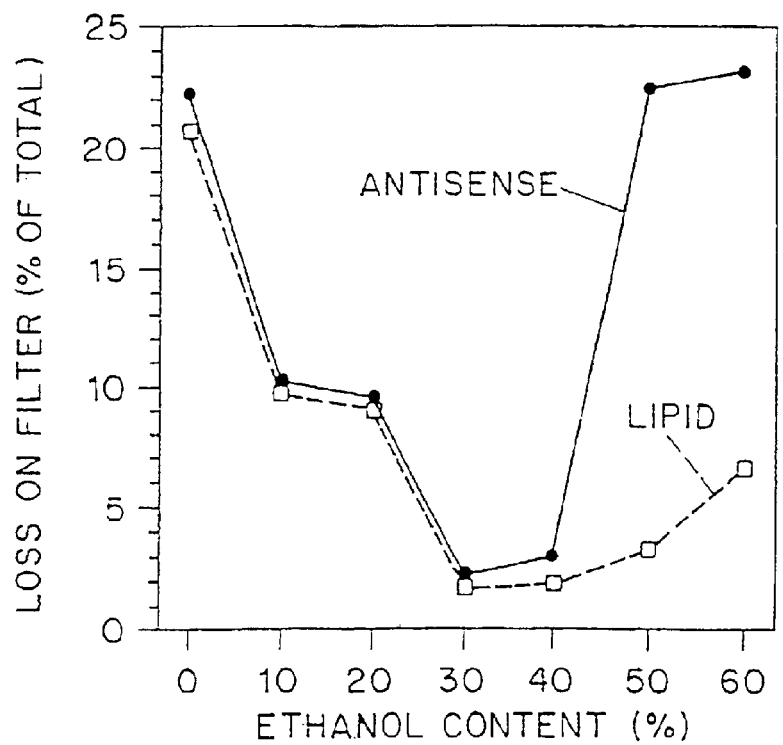
FIG. 2 illustrates the influence of ethanol on lipid and antisense loss during extrusion. The liposomal antisense compositions were prepared as described for FIG. 1. The samples were extruded ten times through three 100 nm filters as described in "Materials and Methods". After extrusion, the filters were analyzed for [$^3$H]-antisense and [$^{14}$C]-lipid radioactivity by standard scintillation counting techniques. Results were expressed as a percent of the total initial radioactivity.

FIG. 1 demonstrates the effects of ethanol on the encapsulation of antisense at pH 3.8. The encapsulation efficiency of phosphorothioate antisense increases in a near linear manner up to a final ethanol concentration of 50%, vol/vol. At an ethanol content greater than 50%, a large amount of aggregation/precipitation is observed. The effect of ethanol on vesicle formation can be further observed by monitoring both lipid and antisense loss on the filters during extrusion (FIG. 2). At low ethanol contents, extrusion is slow and the proportion of lipid and antisense loss is the same, suggesting that the losses are due to the formation of large complexes which get trapped on the filter. At ethanol contents of 30 and 40%, extrusion is very quick and losses of both lipid and antisense are minimal. As the ethanol content is increased above 40%, the loss of antisense becomes disproportionally high relative to the lipid. This can be attributed to the insolubility of DNA in high concentrations of alcohol. Furthermore, in the presence of ethanol, PEG is required to prevent aggregation and fusion of the vesicles (results not shown).

EXAMPLE 2

This example illustrates the effects of DODAP on the encapsulation of antisense, and further illustrates the effect of initial antisense concentration on the compositions.

Figure 3:
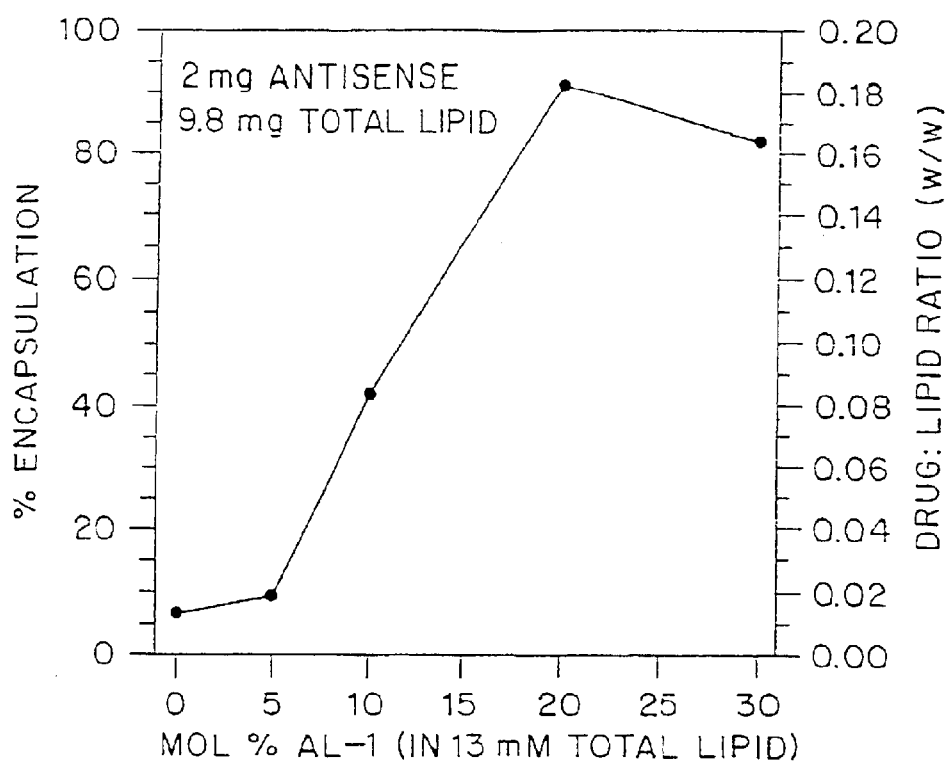
FIG. 3 illustrates the influence of DODAP content on the encapsulation of antisense oligodeoxynucleotides. A 0.6 mL aliquot of a [$^3$H]-phosphorothioate antisense oligodeoxynucleotide (in 300 mM citrate buffer, pH 3.80) was mixed with 0.4 mL of a 95% ethanol solution of lipid (DSPC:CHOL:DODAP:PEG-CerC14; 100–(55+X):45:X: 10, molar ratio) at final concentrations of 2 mg/mL and 9.9 mg/mL, respectively. The molar ratio of DODAP was varied between 0 and 30%. The molar ratio of DSPC was adjusted to compensate for the changes in DODAP content. Encapsulation was assessed either by analyzing the pre-column and post-column ratios of [$^3$H]-antisense and [$^{14}$C]-lipid or by determining the total pre-column and post-column [$^3$H]-antisense and [$^{14}$C]-lipid radioactivity.
Figure 4:
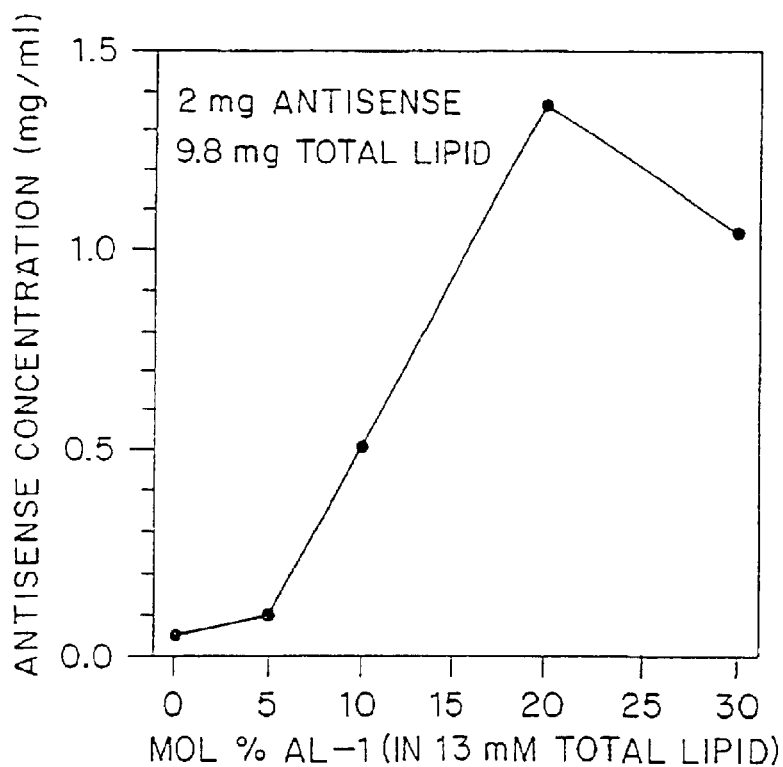
FIG. 4 illustrates the influence of DODAP content on the encapsulation of antisense oligodeoxynucleotides. Samples were identical to those prepared in FIG. 3. In this instance, the amount of antisense associated with the lipid was assessed by a solvent extraction procedure as described in "Material and Methods". Antisense was extracted into a methanol:water aqueous phase, while the lipid was soluble in the organic (chloroform) phase. The aqueous phase was preserved and antisense concentration was determined by measuring the absorbance at 260 nm. This confirmed that the antisense was associated with the lipid vesicles, and that the [$^3$H]-label on the antisense had not exchanged to the lipid.

Having demonstrated that ethanol can greatly facilitate the preparation of lipid vesicles containing entrapped antisense, the next step was to examine the influence of DODAP (AL-1) content on the encapsulation of antisense (FIG. 3). Accordingly, a 0.6 mL aliquot of a [$^3$H]-phosphorothioate antisense oligodeoxynucleotide (in 300 mM citrate buffer, pH 3.80) was mixed with 0.4 mL of a 95% ethanol solution of lipid (DSPC:CHOL:DODAP:PEG-CerC14; 100−(55+X):45:X:10, molar ratio) at final concentrations of 2 mg/mL and 9.9 mg/mL, respectively. The molar ratio of DODAP was varied between 0 and 30%. The molar ratio of DSPC was adjusted to compensate for the changes in DODAP content. The samples were extruded ten times through three 100 nm filters as described in "Materials and Methods", and were dialyzed for 2–3 hours in 300 mM citrate buffer, pH 3.80, to remove a majority of the excess ethanol. The samples were switched to HEPES-buffered saline (HBS), pH 7.50, and dialyzed for a minimum of 12 hours to replace the external citrate buffer with HBS. Non-encapsulated antisense was then removed from the liposomal antisense by DEAE-sepharose chromatography as described in "Material and Methods". Encapsulation was assessed either by analyzing the pre-column and post-column ratios of [$^3$H]-antisense and [$^{14}$C]-lipid or by determining the total pre-column and post-column [$^3$H]-antisense and [$^{14}$C]-lipid radioactivity. As seen in FIG. 3, antisense encapsulation increased significantly between 5–20% DODAP. At DODAP contents greater than 20–25%, extrusion of the vesicles became more difficult suggesting the formation of complexes. At DODAP concentration of 40 and 50%, extrusion of the lipid/antisense mixture took hours compared to minutes for a lipid composition containing 20% DODAP. To verify that the antisense was indeed associated with the lipid and that the observed encapsulation was not due to exchange of the [$^3$H]-label from the antisense onto the lipid, the antisense was extracted from the lipid using a Bligh and Dyer extraction. Using this technique, the antisense, which is soluble in the aqueous phase, was separated from the lipid (soluble in the organic phase) and quantified by measuring the absorbance at 260 nm (FIG. 4). While this method can underestimate the antisense concentration, the technique substantiated that the observed association of antisense with the lipid was not an artifact.

In yet another experiment, varying concentrations of a 20mer of [$^3$H]-phosphoro-thioate antisense oligodeoxynucleotide (in 300 mM citrate buffer, pH 3.80) were mixed with an ethanol solution of lipid (DSPC:CHOL:DODAP:PEG-CerC14; 25:45:20:10, molar ratio), 9.9 mg/mL (final concentration). The samples were extruded and dialyzed twice as described above. Non-encapsulated antisense was then removed from the liposomal antisense by DEAE-sepharose chromatography as described in "Material and Methods". Encapsulation was assessed either by analyzing the pre-column and post-column ratios of [$^3$H]-antisense and [$^{14}$C]-lipid or by determining the total pre-column and post-column [$^3$H]-antisense and [$^{14}$C]-lipid radioactivity. EPC:CH liposomes containing encapsulated antisense are included for comparison.

Figure 6:
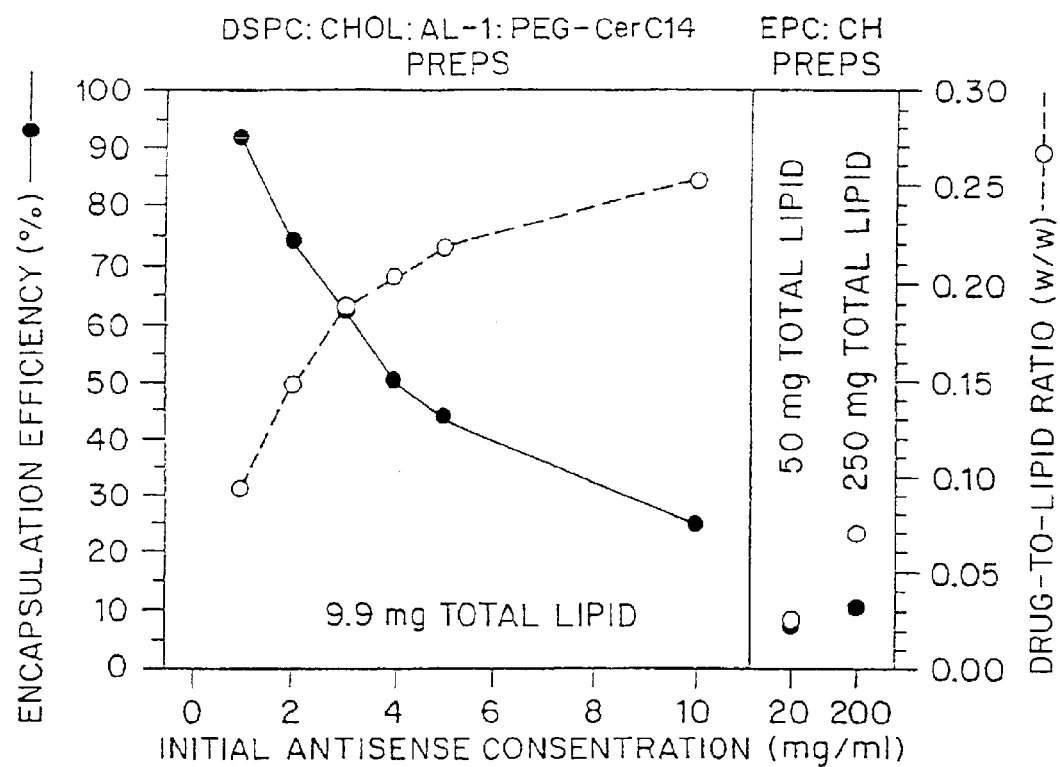
FIG. 6 illustrates the influence of the initial antisense concentration on antisense loading in DODAP vesicles. Varying final concentrations of a 20mer of [$^3$H]-phosphorothioate antisense oligodeoxynucleotide (in 300 mM citrate buffer, pH 3.80) were mixed with an ethanol solution of lipid (DSPC:CHOL:DODAP:PEG-CerC 14; 25:45:20:10, molar ratio), 9.9 mg/mL (final concentration). Encapsulation was assessed either by analyzing the pre-column and post-column ratios of [$^3$H]-antisense and [$^{14}$C]-lipid or by determining the total pre-column and post-column [$^3$H]-antisense and [$^{14}$C]-lipid radioactivity. EPC:CHOL liposomes containing encapsulated antisense are included for comparison.

Optimization of the drug:lipid ratio was accomplished by increasing the initial antisense concentration that was mixed with 9.8 mg total lipid (DSPC:CHOL:DODAP: PEG-CerC14; 25:45:20:10) (FIG. 6). Drug:lipid ratios of up to 0.25, w/w, were obtained using 10 mg/mL of antisense in the preparation. However, the increased drug:lipid ratio was accompanied by a decrease in encapsulation efficiency, therefore a compromise must be made between optimizing the drug:lipid ratio and encapsulation efficiency. In comparison, antisense encapsulated by hydration of a dry lipid film (i.e. EPC:CHOL) in the absence of cationic lipid typically yields low encapsulation efficiencies (<12–15%) and drug:lipid ratios (<0.1, w/w). Consequently, significant quantities of antisense are wasted during the encapsulation procedure.

EXAMPLE 3

This example illustrates the properties of the liposomal antisense formulations provided in the Materials and Methods above.

The size distribution of a liposomal preparation of antisense was determined by quasi-elastic light scattering (QELS) immediately after removal of the free antisense (A), and after storage of the preparation for 2 months at 4° C. (B), using a Nicomp Model 370 sub-micron particle sizer. A 0.6 mL aliquot of a [$^3$H]-phosphorothioate antisense oligodeoxynucleotide (in 300 mM citrate buffer, pH 3.80) was mixed with 0.4 mL of a 95% ethanol solution of lipid (DSPC:CHOL:DODAP:PEG-CerC14; 25:45:20:10, molar ratio) at final concentrations of 2 mg/mL and 9.9 mg/mL, respectively. The sample was extruded ten times through three 100 nm filters as described in "Materials and Methods", and dialyzed for 2–3 hours in 300 mM citrate buffer, pH 3.80, to remove a majority of the excess ethanol. The sample was switched to HEPES-buffered saline (HBS), pH 7.50, and dialyzed for a minimum of 12 hours to replace the external citrate buffer with HBS. Non-encapsulated antisense was then removed from the liposomal antisense by DEAE-sepharose chromatography as described in "Material and Methods".

The size distribution and storage stability of antisense preparations described herein is demonstrated in FIG. 5. The size distribution of a standard DSPC:CHOL:DODAP:PEG-CerC14 (25:45:20:10) preparation containing a 2 mg/mL initial antisense concentration was analyzed immediately after column chromatography to remove any free antisense. A very homogenous distribution is observed after preparation (119±32 nm). This size distribution remained stable for at least 2 months after storage at 4° C. (119±32 nm).

EXAMPLE 4

This example illustrates the clearance pharmacokinetics, biodistribution and biological activity of an encapsulated murine ICAM-1 phosphorothioate antisense oligodeoxynucleotide.

4.1 Plasma Clearance

Encapsulated liposomal antisense was prepared using the ethanol-citrate procedure as described in "Material and Methods". Initial lipid and antisense concentrations were 9.9 and 2 mg/mL, respectively. Liposomal formulations were composed of X:CHOL:DODAP:PEG-CerC14 (25:45:20:10), where X represents either distearoylphosphatidylcholine (DSPC), sphingomyelin (SM), or palmitoyloleoylphosphatidylcholine (POPC). The formulations contained a lipid label ([$^{14}$C]-cholesterylhexadecylether) and [$^3$H]-antisense and were injected (200 µL) intravenously via the lateral tail vein of female (2025 g) ICR mice at a lipid dose of 120 mg/kg. Blood was recovered by cardiac puncture on anesthetized mice. Lipid and antisense recoveries were determined by standard scintillation counting techniques.

Figure 7:
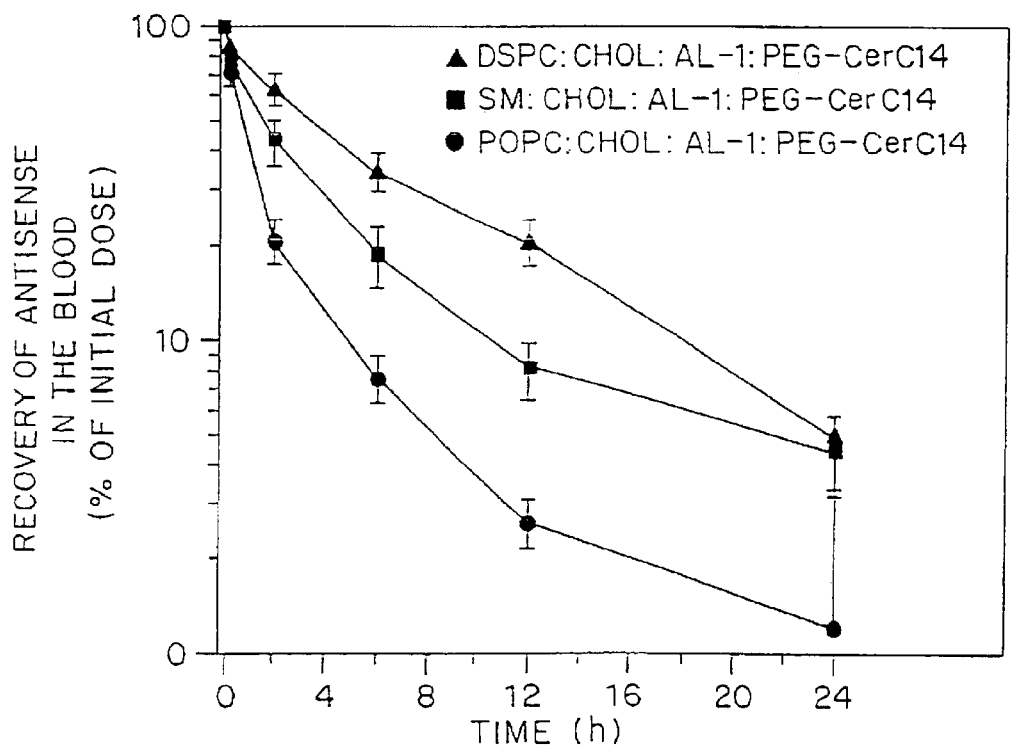
FIG. 7 illustrates the plasma clearance of encapsulated antisense. Encapsulated liposomal antisense was prepared using the ethanol-citrate procedure as described in "Material and Methods". Initial lipid and antisense concentrations were 9.9 and 2 mg/mL, respectively. Liposomal formulations were composed of X:CHOL:DODAP:PEG-CerC14 (25:45:20:10), where X represents either distearoylphosphatidylcholine (DSPC), sphingomyelin (SM), or palmitoyloleoylphosphatidylcholine (POPC). The formulations contained a lipid label ([$^{14}$C]-cholesterylhexadecylether) and [$^3$H]-antisense and were injected (200 µL) intravenously via the lateral tail vein of female (20–25 g) ICR mice at a lipid dose of 120 mg/kg. Blood was recovered by cardiac puncture on anesthetized mice. Lipid and antisense recoveries were determined by standard scintillation counting techniques.

The plasma clearance of three formulations, DSPC-:CHOL:DODAP: PEG-CerC14, SM:CHOL:DODAP:PEG-CerC14, and POPC:CHOL:DODAP:PEG-CerC14, of encapsulated antisense were examined in inflamed ICR mice (FIG. 7). The circulation time was longest for the DSPC version of the formulation.

4.2 Organ Accumulation

Liposomal antisense compositions were prepared and administered to mice as outlined in the preceding section. Mice were terminated by cervical dislocation and the organs were recovered and processed as described in "Materials and Methods". Lipid and antisense recoveries were determined by standard scintillation counting techniques.

Figure 8:
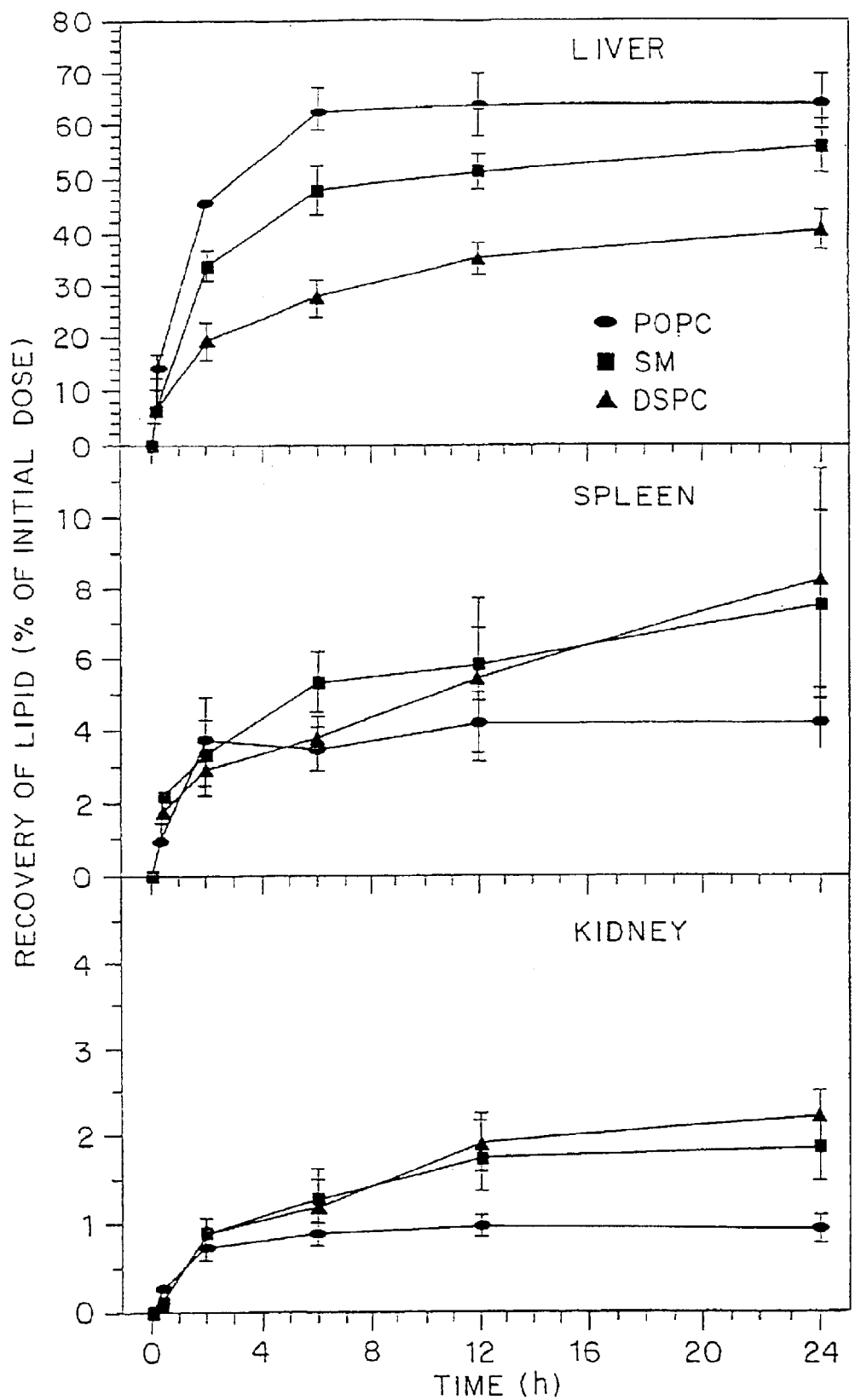
FIG. 8 illustrates the biodistribution of encapsulated antisense. Encapsulated liposomal antisense was prepared using the ethanol-citrate procedure as described in "Material and Methods". Initial lipid and antisense concentrations were 9.9 and 2 mg/mL, respectively. Liposomal formulations were composed of X:CHOL:DODAP:PEG-CerC14 (25:45:20:10), where X represents either distearoylphosphatidylcholine (DSPC), sphingomyelin (SM), or palmitoyloleoylphosphatidylcholine (POPC). The formulations contained a lipid label ([$^{14}$C]-cholesterylhexadecylether) and [$^3$H]-antisense and were injected (200 µL) intravenously via the lateral tail vein of female (20–25 g) ICR mice at a lipid dose of 120 mg/kg. Mice were terminated by cervical dislocation and the organs were recovered and processed as described in "Materials and Methods". Lipid and antisense recoveries were determined by standard scintillation counting techniques.

Organ accumulation of the various formulations was typical of previously described liposome clearance patterns, with the RES organs, principally the liver and spleen, being responsible for the majority of clearance (FIG. 8). One interesting observation is that the liver and spleen clearance account for only 4045% of the total clearance of the "DSPC" formulation, suggesting that a significant population of vesicles is accumulating in another organ system or is being excreted.

4.3 Stability.

Liposomal antisense compositions were prepared and administered to mice as outlined in the preceding section. Blood was recovered by cardiac puncture on anesthetized mice. Lipid and antisense recoveries were determined by standard scintillation counting techniques. Release rates were determined by measuring the [3H]/[14C] ratio over time.

Figure 9:
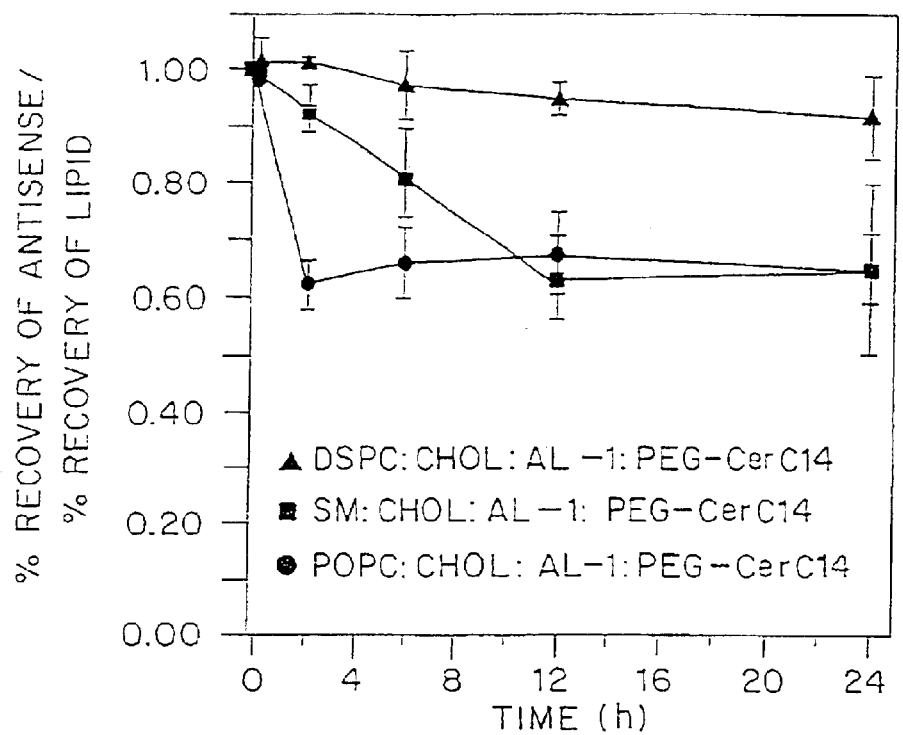
FIG. 9 illustrates the differential release rates of antisense in plasma. Encapsulated liposomal antisense was prepared using the ethanol-citrate procedure as described in "Material and Methods". Initial lipid and antisense concentrations were 9.9 and 2 mg/mL, respectively. Liposomal formulations were composed of X:CHOL:DODAP:PEG-CerC14 (25:45:20:10), where X represents either distearoyl-phosphatidylcholine (DSPC), sphingomyelin (SM), or palmitoyloleoylphosphatidylcholine (POPC). The formulations contained a lipid label ([$^{14}$C]-cholesterylhexadecylether) and [$^3$H]-antisense and were injected (200 µL) intravenously via the lateral tail vein of female (20–25 g) ICR mice at a lipid dose of 120 mg/kg. Blood was recovered by cardiac puncture on anesthetized mice. Lipid and antisense recoveries were determined by standard scintillation counting techniques. Release rates were determined by measuring the [3H]/[14C] ratio over time.

The stability of the formulations was also assessed by measuring the ratio of antisense and lipid recovery in the blood at various times (FIG. 9). A ratio of 1.0 suggests that the antisense and the lipid are staying together in the circulation. The "DSPC" formulation showed little deviation from a ratio of 1.0 over 24 h, suggesting that it is very stable in the circulation. The "POPC" formulation dropped to a ratio of 0.6 after 2 h, while the ratio for the "SM" formulation decreased more slowly, reaching 0.6 after 12 h in the circulation. These results indicate that it may be possible to deliberately alter the antisense release rates by modifying the lipid composition.

4.4 PEG-Acyl Influence on Circulation Half-Life of Single Dose of Thioate Antisense Encapsulated lipid-encapsulated antisense was prepared using the ethanol-citrate procedure as described in "Material and Methods". Initial lipid and antisense concentrations were 9.9 and 2 mg/mL, respectively. Liposomal formulations were composed of DSPC:CHOL:DODAP:PEG-CerC14 or C20 (25:45:20:10). The formulation contained a lipid label ([$^{14}$C]-cholesterylhexadecylether) and [$^{3}$H]-antisense and were injected (200 μL) intravenously via the lateral tail vein of female (20–25 g) ICR mice at a lipid dose of 120 mg/kg. Blood was recovered by cardiac puncture on anesthetized mice. Lipid and antisense recoveries were determined by standard scintillation counting techniques.

The influence of PEG-acyl chain length on clearance rates of a DSPC:CHOL:DODAP:PEG-Cer formulation was investigated using PEG-CerC14 and PEG-CerC20 (FIG. 10). The inclusion of PEG-CerC20 in the formulation resulted in enhanced circulation times over the PEG-CerC14. This corresponds to in vitro data suggesting that the C14 version of the PEG is exchanged much more rapidly out of the vesicle than the C20 version.

4.5 In Vivo Efficacy of Single Dose of Lipid Encapsulated ICAM-1 (Phosphorothioate) Antisense The efficacy of PS-3082 encapsulated in various lipid formulations containing DODAP was tested in an ear inflammation model using ICR mice.

Inflamed mice were treated at the time of ear challenge with a 30 mg/kg i.v. dose of either HBS (no oligo), EPC:CHOL liposomes with entrapped PS-3082 (identified as AS 1000), POPC:CHOL:DODAP:PEG-CerC14 with entrapped PS-3082 (identified as AS 4100), or DSPC:CHOL:DODAP:PEG-CerC14 with entrapped PS-3082 (identified as AS 4200). Ear swelling was measured at 24 hours after initiating inflammation using an engineer's micrometer.

Ear swelling measurements were made 24 hours after initiating inflammation in mice treated i.v. at the time of ear challenge with either HBS (control), PS-3082 encapsulated in EPC:CHOL vesicles (30 mg/kg dose of oligo), PS-3082 encapsulated in POPC:CHOL:DODAP:PEG-CerC14 vesicles (30 mg/kg dose of oligo), or PS-3082 encapsulated in DSPC:CHOL:DODAP:PEG-CerC14 vesicles (30 mg/kg dose of oligo) (FIG. 11). The "DSPC" formulation resulted in the greatest efficacy, exhibiting only 10% increase in ear swelling over pre-challenge values. A similar trend was observed for cellular infiltration into the "challenged" ear versus the non-treated ear (FIG. 12).

In another evaluation, mice received 10 μCi of [$^{3}$H]-methylthymidine, i.p., 24 hours before initiating inflammation. Inflamed mice were treated at the time of ear challenge with a 30 mg/kg i.v. dose of either HBS (no oligo), EPC-:CHOL liposomes with entrapped PS-3082 (identified as AS 1000), POPC:CHOL:DODAP:PEG-CerC14 with entrapped PS— 3082 (identified as AS 4100), or DSPC:CHOL:DODAP:PEG-CerC14 with entrapped PS— 3082 (identified as AS 4200). Cell infiltration was monitored by measuring the radioactivity in the "challenged ear" versus the non-treated ear. Results are expressed as the ratio of radioactivity in the left (challenged ear) versus right ear.

4.6 In Vivo Efficacy of Single Dose of Lipid Encapsulated ICAM-1 (Phosphodiester) Antisense This experiment demonstrates the in vivo efficacy of a phosphodiester antisense oligodeoxynucleotide encapsulated in lipid particles according to the invention. In specific, the phosphodiester was targeted to the ICAM-1 gene in an ear inflammation model.

| Group | Test Sample/Drug | Dose | Time Point |
|---|---|---|---|
| 1 | control inflammation - HBS | 200 μl | 24 hr |
| 2 | corticosteroid | 200 μl | 24 hr |
| 3 | empty vesicles | 200 μl | 24 hr |
| 4 | PS-3082 | 200 μl | 24 hr |
| 5 | PO-3082 | 200 μl | 24 hr |

Antisense Sample Preparation: Antisense was encapsulated using the standard methods of Examples 5–9, using the phosphodiester modification. The phosphodiester formulation used 10–50 mM citrate (preferably 20 mM citrate), pH 4.0 instead of 300 mM citrate, pH 4.0 preferred for a phosphorothioates. Empty vesicles consisted of lipid components only. Corticosteroid (either Halobetasol propionate 0.05% by weight (Westwood Squibb, Montreal) or Dexamethasone (50 ug dissolved in 4:1 acetone:olive oil)) was applied topically in a thin film to cover the surface of the ear 15 minutes after ear challenge.

Inflammation and Dosing: Mouse ear inflammation was induced using DNFB as described above in Materials and Methods. Female ICR mice (6–8 weeks old) received intravenous tail vein injections of antisense (200 μl). Antisense doses for the phosphorothioate and phosphodiester antisense were adjusted to be 20–30 mg/kg. 6 mice were tested with each formulation. Administration occurred 15 min. after the application of 0.2% DNFB to the mouse ear. Ear measurements were made on anaesthetized mice 24 hours after treatment (unless shown otherwise) and prior to termination. Mice are terminated by cervical dislocation and the ears are removed around the pinna. Ears are then weighted, digested (Solvable) and analyzed for radioactivity by liquid scintillation counting. Ears were analyzed for 1) Ear edema—based on the increase in ear thickness due to ear swelling. Calculated by subtracting pre-ear thickness values from post-ear thickness values FIG. 19. 2) Cell infiltration—based on radioactivity accumulated in the inflamed (right) ear vs. the control (left) ear FIG. 20; and 3) Ear weights—left ear versus right ear (measurement of edema) FIG. 21.

Results: The controls consisting of buffer alone (HBS) or Empty Vesicles alone demonstrated no efficacy. Topical corticosteroid demonstrates its known excellent efficacity by reducing inflammation to below pre-challenge levels. Both the phosphorothioate and phosphodiester antisense show excellent efficacy through a systemic delivery administration, reducing the degree of inflammation by around 70% and 85%, respectively. Thus, it is possible to administer the compositions of the invention at a site where the disease site is distal to the site of the injection.

4.7 In Vivo Efficacy of US3 Antisense (Tumor Window Model)

In this example, the anti-tumor activity of lipid encapsulated US3, an antisense oligonucleotide directed at the erb-β-2 gene, has been demonstrated in an in vivo human breast tumor model.

The human breast carcinoma line MDA-MB453 was implanted in a mouse tumor window model according to the method of Wu, N. Z., Da, D., Rudoll, T. L., Needham, D., Whorton, R. & Dewhirst, M. W. 1993. Increased microvascular permeability contributes to preferential accumulation of Stealth liposomes in tumor tissue. Cancer Research 53: 3765–3770; and Dewhirst, M. W., Tso, C. Y., Oliver, R., Gustafson, C. S., Secomb, T. W. & Gross, J. F. 1989. Morpholigic and hemodynamic comparison of tumor and healing normal tissue microvasculature. Int. J. Radiat. Oncol. Biol. Phys. 17: 91–99. See also Dewhirst, MW., and Needham, D. 1995. Extravasation of Stealth Liposomes into Tumors: Direct Measurement of Accumulation and Vascular Permeability using a Skin Flap Window Chamber. In Stealth Liposomes (Eds. Lasic, D. and Martin, F.) CRC Press.

The lipid-antisense formulation consists of disteroylphosphatidylcholine (DSPC, 25 mol %), cholesterol (Chol, 45 mol %), dioleoylphosphatidyldiaminopropane, (DODAP, or AL1, 20 mol %) and PEG-ceramide (C14 chain length, 10 mol %). For some experiments detailed below, proportions and constituents were altered, but the method of preparation remained the same. Lipids were dissolved in ethanol at 20 mg/ml (PEG-ceramide at 50 mg/ml). Routinely, 1 to 2 $\mu$Ci $^{14}$C-cholesterylhexadecylether was added as a lipid radiolabel. Lipids were mixed in the correct proportions in ethanol to a final concentration of 10 mg in 400 ll. The lipid mixture was then added dropwise to phosphorothioated antisense (US3: anti-human erb-B-2 GGT GCT CAC TGC GGC (SEQ ID. No 3) dissolved in 300 mM citrate buffer pH 4.0 (600 ll to make a final volume of 1 ml). The antisense was used at a variety of concentrations, but the optimum concentration for maximum encapsulation efficiency and drug:lipid ratio was determined to be 0.5 mg/ml final. During the addition, the solution becomes opaque. The DODAP is positively charged at pH 4.0 (pKa=6.53) and so attracts the negatively charged DNA molecules. The mixture was subjected to five cycles of freezing in liquid $N_2$ and thawing at 65° C. followed by extrusion through 100 nm filters ten times at 65° C.

After extrusion, two methods can be used for removal of the external antisense. Firstly, the liposomes are diluted 2:1 with citrate (to reduce ethanol content to 20%) then applied to a Bio-Gel A18M 100–200 mesh column equilibrated with HBS. The column profiles shown in this report were generated in this manner. Alternatively, the liposomes are dialyzed 2 h against citrate to remove ethanol, the overnight against HBS to increase the external pH. The resulting mixture is then applied to a DEAE cation exchange column to remove external oligo. This method was the routine method used for sample preparation for in vivo studies. Antisense concentrations were routinely determined by A260 measurements. Lipid concentrations were determined by scintillation counting after spiking initial mixture with a known concentration of $^3$H or $^{14}$C cholesterylhexadecyl ether, or by HPLC. Encapsulation efficiency was determined by division of the final drug to lipid ratio by the initial drug to lipid ratio.

In vivo efficacy evaluation: When the tumor in the window has reached a diameter of 2–3 mm, treatment with free or TCS-encapsulated US3 oligonucleotide is initiated. Treatment consists of a 200 ul intravenous administration (tail vein) of either free US3 or TCS-encapsulated US3 on a 3 administrations/week schedule and an antisense dose of 10 mg/kg/administration. Tumor size is monitored 3 times per week by microscopy.

Results: The TCS-encapsulated US3 oligonucleotide was very effective at preventing the growth, or causing extensive size reduction, of the MDA-MB-453 human breast carcinoma in the window model. In contrast, unencapsulated oligonucleotide was ineffective at inhibiting tumor growth.

4.8 In Vivo Clearance of Various Formulations Using Alternative Amino Lipids: DODAP or DODMA Antisense particle formulations were prepared according to Example 2, with the following modifications: In assay#1 and #2, 25% AL-1 (hydrochloride salt of DODAP) and 25% free base DODAP were employed, respectively, with a concomitant reduction in the amount of DSPC. Assay#3, 4 and 5 employed 30%, 25% and 20% DODMA (free base (prepared at Inex Pharmaceuticals Corp., Burnaby BC)), respectively, again with a concomitant reduction of DSPC.

Both the encapsulation efficiency and in vivo clearance of the formulations were studied. There was no significant difference between the encapsulation or clearance of the free base or HCl salt of DODAP. Decreasing DODMA concentration (30, 25, 20%) severely decreased the encapsulation efficiency of PS-2302 (91%, 43%, 35%) and likewise the Drug/Lipid ratio of the resulting formulation.

In the clearance study outlined in FIG. 14, DODMA formulations demonstrated slightly higher rates of clearance than 25% DODAP or AL-1, although all formulations appear to be retained in the circulation to a degree which is suitable for human therapeutics.

4.9 PEG-Acyl Influence on Clearance Rate of Repeat Doses of Encapsulated EGF-R Phosphorothioate Antisense Lipid-encapsulated antisense was prepared using the ethanol-citrate procedure as described above, with changes to molar ratios of components as indicated. Initial lipid and antisense concentrations were about 9.9 and 2 mg/mL, respectively. DODAP containing formulations had drug:lipid ratios of 0.15 (+/−) 0.05. Passive encapsulation systems had drug lipid ratios of 0.03. Nine different liposomal formulations were prepared, using standard techniques, in the following molar ratios:

| Formulation | DSPC (mol %) | Chol (mol %) | DODAP (mol %) | Steric Barrier Derivatized Lipid (name: mol %) | Antisense (EGF-R 2 mg/ml) |
|---|---|---|---|---|---|
| 1 | 55 | 45 | Nil | Nil | Empty |
| 2 | 50 | 45 | Nil | ATTA8-DSPE: 5 | Empty |
| 3 | 50 | 45 | Nil | ATTA8-DSPE: 5 | AS |
| 4 | 20 | 45 | 30 | ATTA8-DSPE: 5 | AS |
| 5 | 20 | 45 | 30 | PEG-DSPE: 5 | AS |
| 6 | 25 | 45 | 25 | PEG-CerC14: 5 | Empty |
| 7 | 25 | 45 | 25 | PEG-CerC14: 5 | AS |
| 8 | 25 | 45 | 25 | PEG-CerC20: 5 | Empty |
| 9 | 25 | 45 | 25 | PEG-CerC20: 5 | AS |

Antisense ("AS") used was fully phosphorothioated EGFR (anti-human Epidermal Growth Factor Receptor) CCG TGG TCA TGC TCC (SEQ ID. No 10) (prepared by Hybridon, Inc.)

PEG-CerC14 is PEG(mw2000)—Ceramide with 14 carbon acyl chain.

PEG-CerC20 is PEG(mw2000)—Ceramide with 20 carbon acyl chain.

PEG-DSPE is PEG(mw2000)—1,2-distearoyl-sn-glycero-3-phosphoethanolamine

ATTA8-DSPE is N-(ω-N'-acetoxy-octa(14' amino-3',6',9',12'-tetraoxatetradecanoyl))-1,2-diastearoyl-sn-glycero-3-phosphoethanolamine (molec weight about 2660). Synthesis of ATTA8-DSPE is fully disclosed in U.S. Provisional Pat. Application Ser. No. 60/073,852, filed 23 Dec. 1997 and U.S. Provisional Pat. Application Ser. No. 60/073,852 filed 2 Feb. 1998 both assigned to the assignee of the instant invention and incorporated herein by reference.

Each formulation contained a lipid label ($[^{14}C]$-cholesterylhexadecylether) and $[^{3}H]$-antisense, as described in Example 4.4, above. All samples were prepared in 300 mM citrate pH 4.0 containing 40% ethanol and extruded 10×through 100 nm filters. Formulations contained phosphorothioate antisense and lipid or empty lipid alone. Samples were dialyzed in HBS (20 mM Hepes, 145 mM NaCl, pH 7.45) to remove ethanol and citrate. Sample lipid concentrations were adjusted such that the injected lipid dose will be 1.8 μmol/mouse/week (5–10 mg AS per kg mouse/week). Samples were filtered (0.22 lam) prior to injection.

In this experiment female (20–25 g) ICR mice (68 weeks old) were divided into 9 groups of 6, plus other control groups. Each group received four injections of the same formulation. All injections were 200 μL intravenous (via the lateral tail vein) at a lipid dose of 120 mg/kg. Mice were dosed every week for 3 weeks (4 injections). At 4 weeks, certain groups (treated with lipid and antisense) were given an injection of empty lipid carriers of varying 4 composition to evaluate whether there is rapid clearance of the carrier in the absence of antisense. Blood (25 μl, pipettor) was collected 1 h post-injection each week for 3 weeks by tail nicks. Mice were weighed each week to estimate blood volume (8.0 ml whole blood/100 g body weight). Blood was placed in a glass scintillation vial containing 200 μl of 5% EDTA. Solvable (500 μl) was added and the blood was digested for 3 h at 65° C. Samples were decolorized by the addition of 100 μl 70% hydrogen peroxide. Samples were analyzed for radioactivity by liquid scintillation counting. At the end of 4 weeks, mice were terminated by $CO_2$ inhalation or cervical dislocation preceded by general anesthesia.

The results of this experiment are shown in FIG. 15. For all formulations not containing antisense ("empty liposomes") repeat dosages demonstrated circulation times reasonably consistent with the first dosage. However, when antisense is used in the formulation, it was surprisingly found that the acyl chain length of the lipid derivatized to the steric barrier (i.e. ATTA or PEG) moiety demonstrates a profound effect on clearance rates. Repeat dosages of PEG-CerC20, PEG-DSPE and ATTA8-DSPE formulations are rapidly cleared from the circulation compared to the first dosage, whereas the PEG-CerC14 formulation is reasonably consistent with the first dosage.

Similar results are demonstrated in FIG. 16. The formulations were identical to those of FIG. 15, with the additional formulation of empty vesicles using the same lipids as formulations 4 and 5.

Without intending to be bound by any particular theory of action, it is suggested by these results that lipids like the PEG-CerC14 lipid, a lipid which exchanges out of the liposome membrane with a T½ on the order of minutes (i.e. 1–60 mins) in blood provides a tremendous benefit over lipids like PEG-CerC20, PEG-DSPE and ATTA8-DSPE which do not exchange out, where repeat dosing of a lipid-formulated compound, such as a therapeutic compound or diagnostic compound, is required. The mammalian blood clearance response may not recognize these as foreign antigens if the derivatized lipid is removed expeditiously from the liposome surface when in circulation. However, when the derivatized-lipid remains with the formulation for extended periods, a clearance response is invoked, which causes rapid clearance upon repeat dosing. This data suggests that any lipid derivatized with a steric barrier molecule that exchanges out of the liposome membrane faster than PEG-CerC20, PEG-DSPE or ATTA8DSPE will be superior for use in repeat dosing. For example ATTA8-DMPE, or PEG-CerC8 to C18 all being exchangeable, will have improved circulation characteristics upon repeat administration.

Taken together, it will be evident to one skilled in the art, that on the basis of these teachings, any diagnostic or therapeutic agent that may be delivered in a lipid formulation comprising a steric-barrier derivatized lipid, such as a PEG-lipid or ATTA-lipid, should be tested with both a long and short acyl-chain anchors, in order to determine which formulation is best for repeat dosings.

Further, without intending to be bound by any theory of action, the invention herein may prove to be particularly useful when the bioactive agent being delivered is a non-cytotoxic agent. Cytotoxic agents kill those cells which clear long circulating (i.e. PEG-DSPE) liposomes. This ensures that repeat dosings will not be rapidly cleared, because the cells responsible (usually macrophages) do not survive. In these situations, the acyl-chain length may not be significant. However, where the bioactive agent is non-cytotoxic, such as in the case of antisense drugs (regardless of chemistry or target), plasmids, proteins, etc., and many conventional drugs, the invention will be useful for repeat dosing.

4.10 In Vivo Efficacy of Repeat Doses of Encapsulated Phosphorothioate c-myc Antisense in an Oncology Model.

In vivo efficacy of repeat injections of using formulations of the invention are shown in a mouse tumor system in FIG. 17. This experiment demonstrated efficacy of the antisense formulated according to the invention in a human oncology model, and showed the importance of PEG-acyl chain length on the efficacy of repeat dosings.

Lipid-antisense particle formulation: Formulations were prepared as described in these Examples.

| Formulation | DSPC (mol %) | Chol (mol %) | DODAP (mol %) | Steric Barrier Derivatized Lipid (name: mol %) | Antisense (c-myc 2 mg/ml) |
|---|---|---|---|---|---|
| HBS Buffer | | | | | Empty |
| AS4200 (c-myc) | 25 | 45 | 25 | PEG-CerC14: 5 | LR-3280 |
| AS4204 (c-myc) | 25 | 45 | 25 | PEG-CerC20: 5 | LR-3280 |
| AS4204 (c-myc SCR) | 25 | 45 | 25 | PEG-CerC20: 5 | c-myc SCR |
| AS4204 (PS-2302) | 25 | 45 | 25 | PEG-CerC20: 5 | PS-2302 |
| AS4204 (PS-3082) | 25 | 45 | 25 | PEG-CerC20: 5 | PS-3208 |
| c-myc | | | | | LR-3280 |
| c-myc SCR | | | | | c-myc SCR |
| PS-2302 | | | | | PS-2302 |
| PS-3082 | | | | | PS-3082 |
| AS4200 (no antisense) | 25 | 45 | 25 | PEG-CerC14: 5 | Empty |

-continued

| Formulation | DSPC (mol %) | Chol (mol %) | DODAP (mol %) | Steric Barrier Derivatized Lipid (name: mol %) | Antisense (c-myc 2 mg/ml) |
|---|---|---|---|---|---|
| AS4204 (no antisense) | 25 | 45 | 25 | PEG-CerC20: 5 | Empty |

Antisense used were:

| LR-3280: | human c-myc gene (phosphorothioate) AAC GTT GAG GGG CAT | (SEQ ID. No 4) |
|---|---|---|
| c-myc SCR: | GAA CGG AGA CGG TTT | (SEQ ID. No 17) |
| PS-2302 | human ICAM-1 (phosphorothioate) GCCCAAGCTGGCATCCGTCA | (SEQ ID. No 2) |
| PS-3082 | murine ICAM-1 (Intracellular Adhesion Molecule-1) (phosphorothioate) TGCATCCCCCAGGCCACCAT | (SEQ ID. No 1) |

Formulations were diluted in filtered HBS, pH 7.6 to achieve required antisense dose (i.e. lipid dose decreases as well). Samples were filtered (0.22 lm) prior to injection. External buffer was HBS (20 mM Hepes, 145 mM NaCl, pH 7.6). Free antisense was dissolved in HBS and adjusted to the required dose by A260 (Extinction coefficients: active and control c-myc=30.6, PS-2302=32.8, PS-3082=33.6).
Tumour Inoculum: B16/BL6 murine melanoma cells were maintained in culture in MEM media supplemented with 10% FBS. On day 0 of the study, $3 \times 10^5$ cells were injected subcutaneously (s.c.) into the dorsal flank (injection volume: 50 $\mu$l) of female C57BL/6 mice (20–23 g). Typically, 15% extra mice will be injected so non-spheroidal tumours or mice in which no tumours are observed can be excluded from the study. Tumours were allowed to grow for a period of 5–7 days until tumors reached 50–100 $mm^3$ prior to initiating treatments with test samples/controls.
Treatment: On the day of first treatment mice with acceptable tumours were randomly grouped with 5 animals per group. Treatment began when tumours were 50–100 mm. Mice were dosed every other day for a total of 7 doses. Administrations were via intravenous tail vein injections (200 ul). Initial drug:lipid ratio of formulation was 0.20 (w/w) and the final drug:lipid ratio (0.14) was held constant; consequently, the lipid concentration varied as samples were diluted to the desired antisense concentration. The antisense dose was 10 mg/kg.
Endpoints: Primary tumour volume was measured using calipers. Length (mm) and width (mm) measurements were made every other day (on non-injection days) for the duration of the study. Tumour height measurements (mm) were made when feasible. Tumour volumes were calculated using the following formulas:
 #1 Tumour Volume $(mm^3)=(L \times W^2)/2$
 #2 Tumour Volume $(mm^3)=(L \times W \times H) \times \pi/6$
Mice were euthanized when tumour volumes reach 10% of body weight or on the first signs of ulceration. Mouse weights were recorded every day during the dosing portion of the study. On termination, all tumours were excised, weighed, observed by FACS analysis or by Northern/Western analysis. Mice were euthanized by $CO_2$ inhalation or cervical dislocation preceded by general anesthesia.
Results: FIG. 7 shows weights of tumors excised and weighed at day 18 for all groups treated with antisense at 10 mg/kg/dose compared with empty lipid controls. Tumour sizes for the AS4200(c-myc) group exhibited the best efficacy and were very consistent with only small ranges in tumour volumes observed (285–451 mm). The group treated with free c-myc also resulted in smaller tumours but exhibited more variability in tumour volume (156–838 $mm^3$). The encapsulated c-myc controls (c-myc SCR/PS-2302/PS-3082), AS4204(c-myc), empty lipid carriers, and free antisense controls, however, showed no inhibitory effect on tumor volumes over the 18 days when compared to HBS controls.
c-myc expression in tumor tissue was also evaluated by FACS. A correlation between tumour size and c-myc protein expression was detected (data not shown).
To determine the importance of the stability of the PEG-polymers, PEG-acyl chain length was evaluated using formulations containing PEG-CerC14 and PEG-CerC20. Interestingly, the formulation containing the PEG-CerC20 (AS4204) showed no apparent efficacy at any of the doses studied. The PEG-CerC14 formulation (AS4200) showed a dose response. The difference observed between the PEG-CerC14 and PEG-CerC20 formulations may reflect the rapid clearance phenomenon that has been observed in other models.
To establish the tolerability of free and encapsulated antisense, mouse weights were measured on a daily basis during the treatment phase of the study. No significant changes in mouse weights for either free or encapsulated formulations were apparent over the course of the dosing phase or throughout the study.

EXAMPLE 5

This example illustrates a high efficiency formulation according to Example 2, but instead of phosphorothioate antisense, employing 1) a phosphodiester antisense compound having exclusively phosphodiester internucleotide linkages (PO-2302 anti-human ICAM-1 GCCCAAGCTG-GCATCCGTCA (SEQ ID. No 1)) prepared by Inex Pharmaceuticals (USA), Inc., Hayward Calif.) or 2) ribozyme molecule to VEGF-R-1 (human Vascular Endothelial Growth Factor Receptor 1) comprising a modified RNA sequence of GAG UUG CUG AUG AGG CCG AAA GGC CGA AAG UCU G (SEQ ID. No 16).
A 15mer of $[^3H]$-phosphodiester antisense oligodeoxynucleotide (PO-2302) in citrate buffer, pH 3.80 (experiments ranged from 10–1000 mM citrate) was mixed with an ethanol solution of lipid (DSPC:CHOL:DODAP:PEG-CerC14; 25:45:20:10, molar ratio) at final concentrations of 2 mg/mL and 9.9 mg/mL, respectively. The final ethanol concentration in the 1 ml preparation was 38% vol/vol. The sample was extruded ten times through three 100 nm filters as described in "Materials and Methods". The sample was dialyzed for 2–3 hours in citrate buffer, pH 3.80 (same molarity as experiment), to remove a majority of the excess ethanol. The samples were switched to HEPES-buffered saline (HBS), pH 7.50, and dialyzed for a minimum of 12 hours to replace the external citrate buffer with HBS. Non-encapsulated antisense was removed either by this regular dialysis, tangential flow dialysis, or chromatography. Encapsulation was assessed either by analyzing the pre-column and post-column ratios of $[^3H]$-antisense and $[^{14}C]$-lipid or by determining the total pre-column and post-column $[^3H]$-antisense and $[^{14}C]$-lipid radioactivity.
FIG. 13 illustrates results. Encapsulation efficiency was over 50% across the 10–50 mM citrate range, and all final (administration ready) drug:lipid ratios were greater than 10% by weight. Parallel experiments varying citrate concentration were conducted with phosphorothioate antisense PS-2302. Results are also above 50% encapsulation, and in fact show a higher encapsulation efficiency than phosphodiesters, particularly at higher citrate concentrations.

This experiment was repeated using 20 mM citrate instead of 300 mM citrate to encapsulate the ribozyme molecule to VEGF-R-1 (human Vascular Endothelial Growth Factor Receptor 1) GAG UUG CUG AUG AGG CCG AAA GGC CGA AAG UCU G (SEQ ID. No 16). FIG. 18 shows the encapsulation efficiency of the ribozyme at was over 50%, approximately the same as the phosphodiester.

EXAMPLE 6

This example illustrates a high efficiency formulation as in Example 5, but replacing DODAP with an alternative protonatable lipid. Typically, the preparation for the alternative will be X:DSPC:CHOL:PEG-CerC14 at 20:25:45:10 molar ratio where X can be DODAC, OA, DODMA or any other lipid suitable for the invention.

Materials: distearoylphosphatidylcholine, DSPC; cholesterol, CHOL (both from Northern Lipids, Vancouver, BC); N,N-dioleyl-N,N-dimethylammonium chloride, DODAC; Oleylamine, OA (prepared by Steve Ansell, Inex); N-(1-(2,3-Dioleoyloxy) propyl)-N,N,-dimethyl ammonium chloride, DODMA (Avanti Polar Lipids, Alabaster AB, chloride salt prepared by Steve Ansell, INEX); poly (ethylene glycol)2000 coupled to a ceramide derivative with 14 carbon acyl chains, PEG-CerC14 (Zhou Wang, INEX Pharmaceuticals); 13×100 mm glass tube; filter sterilized 300 mM citrate buffer, pH 3.9–4.0 (use a 0.2 $\mu$m filter). Fully thioated c-myc antisense (INEX (USA), Hayward Ca), Anhydrous Ethanol (Commercial Alcohols, Toronto, On), Citric acid, Monobasic Sodium phosphate, Dibasic Sodium phosphate, Sodium hydroxide, HEPES (BDH, Mississauga On). Deionized water, Chloroform, Methanol, Oligreen™ oligonucleotide reagent (Molecular Probes, Eugene Or), Sodium chloride, Triton X-100, alcohol dehydrogenase reagent kit, (Sigma Chemical Co., St Louis Mo.), Lipid stock solutions were made in 100% ethanol with the working concentrations of the lipids which is as follows:

DSPC, 20 mg/ml; CHOL, 20 mg/ml (not very soluble above this concentration); DODMA, 20 mg/ml; PEG-CerC14; 50 mg/ml.

To prepare stock solutions of antisense, the antisense molecules were dissolved in the filtered 300 mM citrate buffer at a concentration of 3.33 mg/ml. Lipids were mixed in the desired proportions in a 13×100 mm glass tube to achieve a final volume of 0.4 ml of lipids using 100% ethanol as listed in table 1, below:

TABLE 1

Proportional mixture of lipids in a 13 × 100 mm glass test tube.

| Lipid | Mol % | M. Wt. | mg | $\mu$mol | Stock (mg/ml) | Vol of Stock ($\mu$l) |
|---|---|---|---|---|---|---|
| DODMA | 20 | 652.6 | 1.69 | 2.60 | 20 | 84.5 |
| DSPC | 25 | 790 | 2.57 | 3.25 | 20 | 115 |
| CHOL | 45 | 386.7 | 2.26 | 5.85 | 20 | 113.1 |
| PEG-CerC14 | 10 | 2600 | 3.38 | 1.30 | 50 | 67.6 |
|  | 100 |  | 9.9 | 13.00 |  | 380.2 |

In a separate 13×100 mm glass tube, 0.6 ml of antisense at 3.33 mg/ml was added. The pH of this solution should be 3.9–4.0. (NOTE: the antisense concentration is NOT determined by weight but rather by measuring absorbance at 260 nm). The lipid mixture solution was warmed to 65° C. for about 2 minutes. The antisense tube was vortexed and during this time, using a Pasteur pipette, the lipids (in ethanol) were added slowly in a dropwise manner. The mixture will get "cloudy" and some bubbles maybe observed due to the ethanol, but no aggregates should be present. The resulting volume of the antisense-lipid mixture was 1.0 ml with a 10 mg (13 mmol) total lipid at 13 $\mu$mols, 2 mg of antisense, and 38% ethanol, vol/vol. It can be expected that the pH to rise to about 4.4.

The antisense-lipid mixture was subjected to 5 (five) cycles of freezing in liquid nitrogen and thawing at 65° C. in a waterbath. After each thaw, the mixture was vortexed briefly. Subsequently, the mixture was passed 10 times through three stacked 100 nm polycarbonate filters (Poretics) or extruded using a pressurized extruder apparatus with a thermobarrel attachment (Lipex Biomembranes). The temperature and nitrogen pressure during extrusion were 65° C. and no more than 200 psi to 300 psi, respectively. Each pass should take no more than 2 minutes and is vortexed after each pass.

After extrusion, the mixture was dialyzed in a dialysis tubing (3500 Mwt cutoff; SpectraPor) for 1 hour in 300 mM citrate at pH 3.9–4.0, removing the ethanol. The mixture was transferred into 5 L of HBS buffer at pH 7.5 and allowed to further dialyze to a minimum of 12 hours, to neutralize the DODMA and release any surface bound antisense associated with the vesicles. Alternatively, tangential flow dialysis, ion exchange-chromatography or gel filtration chromatography can be used to process the extruded antisense-lipid mixture to an administration ready preparation.

EXAMPLE 7

This example illustrates a high efficiency formulation as in Example 5, but replacing DSPC with SM to generate a preparation of DODAP:SM:CHOL:PEG-CerC14 at 20:25:45:10 molar ratio. Antisense is processed with the formulation for a standard 1.0 ml volume, which can be scaled up proportionately as required. Materials: Sphingomyelin SM; cholesterol, CHOL; dimethylaminopropane, DODAP; polyethylene glycol coupled to a ceramide derivative with 14 carbon acyl chains, PEG-CerC14; 13×100 mm glass tube; filter sterilized 300 mM citrate buffer, pH 3.9–4.0 (use a 0.2 $\mu$m filter).

Lipid stock solutions were made in 100% ethanol with the working concentrations of the lipids which is as follows:

SM, 20 mg/ml; CHOL, 20 mg/ml (not very soluble above this concentration); DODAP, 20 mg/ml; PEG-CerC14; 50 mg/ml.

To prepare stock solutions of antisense, the antisense molecules were dissolved in the filtered 300 mM citrate buffer at a concentration of 3.33 mg/ml. Lipids were mixed in the desired proportions in a 13×100 mm glass tube to achieve a final volume of 0.4 ml of lipids using 100% ethanol as listed in Table 2, below:

TABLE 2

Proportional mixture of lipids in a 13 × 100 mm glass test tube.

| Lipid | Mol % | M. Wt. | mg | $\mu$mol | Stock (mg/ml) | Vol of Stock ($\mu$l) |
|---|---|---|---|---|---|---|
| DODAP | 20 | 684.5 | 1.78 | 2.60 | 20 | 89.0 |
| SM | 25 | 703 | 2.30 | 3.27 | 20 | 115 |
| CHOL | 45 | 386.7 | 2.26 | 5.85 | 20 | 113.1 |
| PEG-CerC14 | 10 | 2600 | 3.38 | 1.30 | 50 | 67.6 |
|  | 100 |  | 9.72 | 13.02 |  | 384.7 |

In a separate 13×100 mm glass tube, 0.6 ml of antisense at 3.33 mg/ml was added. The pH of this solution should be 3.9–4.0. (NOTE: the antisense concentration is NOT determined by weight but rather by measuring absorbance at 260 nm). The lipid mixture solution was warmed to 65° C. for about 2 minutes. The antisense tube was vortexed and during this time, using a Pasteur pipette, the lipids (in ethanol) were added slowly in a dropwise manner. The mixture will get "cloudy" and some bubbles maybe observed due to the ethanol, but no aggregates should be present. The resulting volume of the antisense-lipid mixture was 1.0 ml with a 10 mg (13 mmol) total lipid at 13 µmols, 2 mg of antisense, and 38% ethanol, vol/vol. It can be expected that the pH to rise to about 4.4.

The antisense-lipid mixture was subjected to 5 (five) cycles of freezing in liquid nitrogen and thawing at 65° C. in a waterbath. After each thaw, the mixture was vortexed briefly. Subsequently, the mixture was passed 10 times through three stacked 100 nm polytcarbonate filters (Poretics) or extruded using a pressurized extruder apparatus with a thermobarrel attachment (Lipex Biomembranes). The temperature and nitrogen pressure during extrusion were 65° C. and no more than 200 psi to 300 psi, respectively. Each pass should take no more than 2 minutes and is vortexed after each pass.

After extrusion, the mixture was dialyzed in a dialysis tubing (3500 Mwt cutoff; SpectraPor) for 1 hour in 300 mM citrate at pH 3.9–4.0, removing the ethanol. The mixture was transferred into 5 L of HBS buffer at pH 7.5 and allowed to further dialyze to a minimum of 12 hours, to neutralize the DODAP and release any surface bound antisense associated with the vesicles. Alternatively, tangential flow dialysis, ion exchange-chromatography or gel filtration chromatography can be used to process the extruded antisense-lipid mixture to an administration ready preparation.

EXAMPLE 8

This example illustrates a high efficiency formulation as in Example 5, but replacing PEG-CerC14 with ATTA8-DSPE to prepare DODAP:DSPC:CHOL:ATTA8-DSPE at 40:10:45:5 molar ratio of antisense formulation.

Materials: distearoylphosphatidylcholine, DSPC; cholesterol, CHOL; dimethylaminopropane, DODAP; N-(ω-N'-acetoxy-octa(14'amino-3',6',9', 12'-tetraoxatetradecanoyl))-1,2-distearoyl-sn-glycero-3-phosphoethanolamine, ATTA8-DSPE; 13×100 mm glass tube; filter sterilized 300 mM citrate buffer, pH 3.9–4.0 (use a 0.2 µm filter).

Lipid stock solutions were made in 100% ethanol with the working concentrations of the lipids which is as follows: DSPC, 20 mg/ml; CHOL, 20 mg/ml (not very soluble above this concentration); DODAP, 20 mg/ml; ATTA8-DSPE; 50 mg/ml.

To prepare stock solutions of antisense, the antisense molecules were dissolved in the filtered 300 mM citrate buffer at a concentration of 3.33 mg/ml. Lipids were mixed in the desired proportions in a 13×100 mm glass tube to achieve a final volume of 0.4 ml of lipids using 100% ethanol as listed in Table 3, below:

TABLE 3

Proportional mixture of lipids in a 13 × 100 mm glass test tube.

| Lipid | Mol % | M. Wt. | mg | µmol | Stock (mg/ml) | Vol of Stock (µl) |
|---|---|---|---|---|---|---|
| DODAP | 40 | 684.5 | 4.16 | 6.08 | 20 | 208 |
| DSPC | 10 | 790 | 1.2 | 1.52 | 20 | 60 |
| CHOL | 45 | 386.7 | 2.6 | 6.72 | 20 | 130 |
| ATTA8-DSPE | 5 | 2638 | 2.0 | 0.76 | 50 | 40 |
|  | 100 |  | 10.26 | 15.1 |  | 438 |

In a separate 13×100 mm glass tube, 0.6 ml of antisense at 3.33 mg/ml was added. The pH of this solution should be 3.9–4.0. (NOTE: the antisense concentration is NOT determined by weight but rather by measuring the absorbance at 260 nm). The lipid mixture solution was warmed to 65° C. for about 2 minutes. The antisense tube was vortexed and during this time, using a Pasteur pipette, the lipids (in ethanol) were added slowly in a dropwise manner. The mixture will get "cloudy" and some bubbles may be observed due to the ethanol, but no aggregates should be present. The resulting volume of the antisense-lipid mixture was 1.0 ml with a 10 mg (13 mmol) total lipid at 13 µmols, 2 mg of antisense, and 38% ethanol, vol/vol. It can be expected that the pH to rise to about 4.4.

The antisense-lipid mixture was subjected to 5 (five) cycles of freezing in liquid nitrogen and thawing at 65° C. in a waterbath. After each thaw, the mixture was vortexed briefly. Subsequently, the mixture was passed 10 times through three stacked 100 nm polytcarbonate filters (Poretics) or extruded using a pressurized extruder apparatus with a thermobarrel attachment (Lipex Biomembranes). The temperature and nitrogen pressure during extrusion were 65° C. and no more than 200 psi to 300 psi, respectively. Each pass should take no more than 2 minutes and is vortexed after each pass.

After extrusion, the mixture was dialyzed in a dialysis tubing (3500 Mwt cutoff; SpectraPor) for 1 hour in 300 mM citrate at pH 3.9–4.0, removing the ethanol. The mixture was transferred into 5 L of HBS buffer at pH 7.5 and allowed to further dialyze to a minimum of 12 hours, to neutralize the DODAP and release any surface bound antisense associated with the vesicles. Alternatively, tangential flow dialysis, ion exchange-chromatography or gel filtration chromatography can be used to process the extruded antisense-lipid mixture to an administration ready preparation.

EXAMPLE 9

This example illustrates use of tangential flow dialysis to clean up a large scale (>50 ml) preparation of extruded antisense-lipid mixture to obtain an administration ready preparation. Tangential Flow Diafiltration has been shown to be useful in four functions in the formulation process 1) buffer exchange, 2) removal of ethanol, 3) removal of unencapsulated antisense and 4) concentration of the formulation. Using TF it is demonstrated that it is possible to efficiently exchange these components using only 10–15 sample volumes with a single buffer system at a very significant reduction in the process time.

Materials for Tangential Flow Dialysis: Microcross Sampler™ Tangential Flow column (Microgon, Laguna Hills, Ca) Masterflex™ console drive and Easyload™ Pump head (Cole-Parmer, Vernon Hills Ill.), Extruder (Lipex Biomembranes, Vancouver BC), Polycarbonate membranes, 100 µm, (AMD Manufacturing, Mississauga On).

Antisense (c-myc) is prepared by dissolving in 300 mM Na Citrate buffer to a final concentration of 4.17 mg/ml for c-myc as verified by absorbance at 260 nm. The antisense stock solution is typically warmed to 65° C. for 2 minutes to dissolve and to remove secondary structure. AS4200 consists of DODAP:DSPC:CHOL:PEG-CER-14 at the percent mol ratio of 25:20:45:10 and the lipids are aliquoted from stock solutions to a total concentration of 10 mg/0.400 ml in anhydrous ethanol. In this study 50–60 ml scale formulations were produced. Thus 20–24 ml of the ethanolic lipid solution is added dropwise, at room temperature, using a peristaltic pump at 1 ml/min into 30–36 ml of the AS solution which is stirring in a 100 ml round bottom flask with a 2 cm magnet stir bar (Stirrer setting 2–3). After mixing, the lipid/antisense suspension was pipetted into a 100 ml extruder prepared with 2–3, 100 μm polycarbonate membranes and pre-equilibrated at 65° C. The suspension was extruded using ten passes at 300 psi. After extrusion the formulation was processed using tangential flow diafiltration.

Tangential Flow Ultrafiltration. A 230 cm² Microcross tangential flow cartridge (50 kDa cut off) was attached to a Masterflex peristaltic pump, sample reservoir and buffer reservoir using Tygon tubing. The tubing length was adjusted so that the total circuit of tubing, pump and TF cartridge had a total dead volume of 30 ml. To this system a 60 ml sample reservoir was attached. The sample was loaded into the tubing and reservoir by running the peristaltic pump at a low speed. After loading, the system was closed and the pump speed gradually increased to the pump maximum (approx. 100 ml/min) until the initial TF cartridge inlet pressure was 12–15 psi and the outlet pressure was 8–11 psi. When the system pressure stabilized, both the filtrate outlet and the buffer reservoir were opened. Opening these valves allowed filtrate to flow out of the cartridge at 10–15 ml/min while wash buffer (i.e. PBS, pH 7.5) was being collected. For a 50–60 ml formulation 700–900 ml of buffer was used to "wash" the sample. Fractions (10 ml) of the filtrate were collected for analysis of ethanol removal, pH, and antisense. After diafiltration was completed the wash buffer reservoir was closed and with the pump continuing to run, filtrate was allowed to flow, concentrating the sample, typically reducing the preparation volume to the tubing dead volume (30–35 ml). The sample was collected from the system and the tubing and column were washed with 15 ml wash buffer to remove any remaining formulation.

Antisense Quantification. Antisense concentration was normally determined by measuring absorbance at 260 nm as outlined in the current protocol. Briefly, antisense stock solutions were quantified by diluting 1:500 in MilliQ water and measuring absorbance. TF filtrate fractions were diluted 1:10 in MilliQ water and absorbance was measured. Antisense in suspension with lipids was measured by adding 10 μl of the suspension to 250 μl MilliQ water. A monophase was created by adding 750 μl CHCl₃/MeOH (2.1:1) and 100 μl MeOH. Immediately after vortexing the mixture the absorbance was measured at 260 nm. In each case the extinction coefficient for the given antisense was multiplied by the dilution factor to determine the antisense concentration.

Lipid Quantification. As outlined in the current protocol, 50 μl aliquots of the lipid/antisense suspension was diluted with 100 μl MilliQ water and submitted for analysis by HPLC. The percent encapsulation efficiency of the formulation is determined by dividing the Drug/Lipid ratio of the finished product by the initial Drug/Lipid ratio formed when the lipid and antisense stock solutions are mixed.

Ethanol Assay. Ethanol in the TF filtrate was determined using an alcohol dehydrogenase reagent kit supplied by Sigma Chemical Co.

DEAE Sephadex chromatography. A suspension of the processed formulation was loaded onto a 1×10 cm column of DEAE sephadex equilibrated in 20 mM PBS, pH 7:5. After eluting through the column the formulation was collected into a sterile falcon tube. The volume, antisense and lipid concentration were measured to determine recovery.

Particle Size. The particle size of the formulation was measured by QELS using a Nicomp Particle sizer, (Nicomp, Santa Barbara, Calif.) and particle sizes are reported in the particle mode with volume weighing.

Results of Large Scale Preparations:

| Assay | Initial Lipid Content (mg/ml) | Initial Antisense Content (mg/ml) | Final Lipid Content (mg/ml) | Final Antisense Content (mg/ml) | Initial Drug: Lipid | Final Drug: Lipid | Encaps. Effic. |
|---|---|---|---|---|---|---|---|
| A | 10.581 | 1.936 | 14.604 | 1.681 | 0.183 | 0.115 | 63% |
| B | 8.727 | 2.284 | 7.926 | 1.008 | 0.262 | 0.127 | 48% |
| C | 11.06 | 2.97 | 2.69 | 0.556 | 0.286 | 0.207 | 77% |

EXAMPLE 10

Phosphodiester and phosphorothioate antisense oligonucleotides encapsulated in according to the methods in Example 2 and 5–9 were examined for their relative susceptibility to nuclease digestion by serum or S1 nuclease. Protection of the phosphodiester-linked oligonucleotide was significantly higher in serum when encapsulated as opposed to the free, raising the $T_{1/2}$ of degradation from 10 mins to at least 8 h. Free phosphorothioate oligodeoxynucleotide showed significant breakdown in serum within 30 minutes, however encapsulated phosphorothioate oligodeoxynucleotide did not show any sign of degradation even after 24 h incubation in serum. In vivo data agrees with these findings, showing no sign of degradation of the encapsulated phosphorothioate antisense until 8 h.

As a positive control, the free phosphodiester and phosphorothioate antisense were subjected to very potent levels of S1 nuclease (100U/50 μg) (1U of S1 nuclease will digest 1 ug DNA per minute at 37° C.). The enzyme completely digested the free phosphodiester and phosphorothioate within seconds after its addition. The encapsulated phosphodiester under the same conditions was over 90% intact at 24 h, and the encapsulated phosphorothioate was fully intact at 24 h.

The experiments were conducted as described in the specification, or modified as follows.

S1 Nuclease Digestion. 50 μg aliquots containing free, encapsulated, or encapsulated+0.5% Triton XI 00 were aliquoted into 1.5 ml eppendorf tubes. To the tubes were added 10 μl 10×S1 nuclease buffer, dH2O (to make final volume 100 μl), and, just prior to digestion, 100U of S1 nuclease to each eppendorf tube. The tubes were sealed with parafilm and incubated at 55° C. A sample of the free, encapsulated, or encapsulated+0.5% Triton X100 not digested by nuclease (standard) was frozen in liquid nitrogen in an eppendorf tube and stored at −20° C. At each desired time point, an aliquot of each sample was collected, added to GDP buffer containing proteinase K (133 μg/ml) and immediately frozen in liquid nitrogen in order to stop the reaction. Once all of the time points were collected, the samples were incubated at 55° C. in a waterbath to activate proteinase K enabling it to denature any remaining S1 nuclease. Proteinase K digested samples were applied to polyacrylamide gels, described below, to assess levels of S1 nuclease degradation Normal Murine/Human Serum Digestion. 50 kg of the free, encapsulated, or encapsulated+0.5% Triton X100 was aliquoted into 1.5 ml eppendorf tubes. To the tubes we added 45 μl normal murine/human serum, dH2O (to make final volume 50 μl), to each eppendorf tube. The tubes were sealed with parafilm and incubated at 37° C. A sample of the free, encapsulated, or encapsulated+0.5% Triton X100 not digested by nuclease (standard) was frozen in liquid nitrogen in an eppendorf tube and stored at −20° C. Aliquots were taken at various time points, added to GDP buffer containing proteinase K (133 μg/ml) and immediately frozen in liquid nitrogen to stop the reaction. Once all of the time points were collected, the samples were incubated at 55° C. in a water-bath to activate proteinase K enabling it to denature any remaining exonuclease. Proteinase K digested samples were applied to polyacrylamide gels to assess levels of exonuclease degradation Micrococcal Nuclease. An alternative standard nuclease assay not employed in the present experiment is the assay disclosed by Rahman et al. U.S. Pat. No. 5,665,710, wherein nucleic acid/lipid particles are incubated for 30 mins at 37° C. in presence of an excess of micrococcal nuclease in 1 mM $CaCl_2$.

Polyacrylamide Gel Electrophoresis (PAGE). Prepared 14 cm×16 cm×7.5 mm polyacrylamide (15% or 20%) gels in 7M urea and TBE. Approximately 300 ng of sample (at each time point) and standard were aliquoted into eppendorf tubes. An equivalent volume of 2× loading buffer was added to each sample. The samples were then heated in a waterbath to 90° C. for 3 min to reduce secondary structures and then applied to the gel. The loaded gel was electrophoresed at 600V for 10 min (to sharpen the band) and then at 300V for the duration of the gel. The gel was incubated in 1× SyberGreen I stain in TBE for a minimum of 15 min and then photographed while illuminated under UV light (3.5 sec exposure, 4.5 aperture).

EXAMPLE 11

Since the lipid particles shown to provide nuclease resistance in the example above contain a poly(ethyleneglycol) surface coating that may sterically shield the surface of vesicles for nuclease activity, $^{31}P$ NMR was used to confirm that the ODN was encapsulated in the interior of the vesicles. FIG. 22 shows spectra obtained from different compositions each containing the same concentrations of c-myc. (Seq. ID. No. 4). When c-myc ODN was free in solution, a sharp $^{31}P$ NMR signal was detected (spectrum 1). However, the signal from the same concentration of c-myc ODN encapsulated in the lipid compositions of the invention was broadened beyond detection under the spectrometer conditions employed. This result can be explained if the entrapped ODN is bound to the interior membrane surface through electrostatic interactions with the cationic form of the inoziable amino lipid (DODAP), and therefore immobilized on the NMR time scale. The aqueous core of the particles is pH 5.5–6.0, a range in which a large proportion of DODAP molecuels will be positively charged. When this transmembrane pH gradient was collapsed and equilibrated to pH 7.4 by the addition of 150 mM ammonium acetate and NaOH to the external buffer, a $^{31}P$ NMR signal for the ODN became apparent (spectrum 3). This is consistent with the internal neutralization of DODAP and the subsequent release of ODN from the membrane surface and into solution where its motion can be detected.

Spectra 4, 6 and 6 demonstrate that the signal in spectrum 3 arises from c-myc PS ODN encapsulated inside the lipid particles. The addition of 5 mM $MnSO^4$ had no effect on the signal intensity (spectrum 4) until the sample was solubilized in 200 mM OGP, after which the $^{31}P$ NMR signal was eliminated (spectrum 5). However, in the absence of $MnSO^4$ solubilization in detergent at pH 7.4 produced two sharp $^{31}P$ NMR signals, once from c-myc ODN free in solution and the other arising from phospholipids in detergent micelles (spectrum 6).

The $^{31}P$ NMR signal intensities for ODN shown in spectra 1 and 6 were the same, however, the signal from the same concentration of encapsulated ODN was attenuated by about 40% (spectra 3 and 4). This is not due to NMR resonance saturation, because the spin-lattice relaxation times ($T_1$) of free ($T_1$=]0.7 s) and encapsulated (T. =2.1 s) ODN at pH 7.4 were essentially the same. The $T_1$ values were measured by an inversion-recovery pulse sequence on samples 1 and 3. Furthermore, the interpulse delay of 3 s for 50° pulses allows for complete relaxation of all ODN resonances. The attenuation of signal intensity shown in spectra 3 and 4 can be attributed to several possibilities, including incomplete solubility of the encapsulated ODN in the aqueous core of the particle, or the existence of secondary ODN-lipid structures within the particle.

EXAMPLE 12

Freeze-fracture electron microscopy and QELS indicated that the compositions of the invention were composed of a homogeneous population of vesicles with a mean diameter of 110±30 nm. The vesicle size distribution was stable for at least 6 months during storage at 4° C. To investigate the potential existence of secondary structure within the vesicles, a cryo-electron microscopy analysis of the particles was performed at 2 different ODN-to-lipid ratios (0.25 and 0.25, w/w (is this really weight to weight or is it molar?) and revealed several interesting features. At the higher ODN-to-lipid ratio, the preparation contained spherical vesicles with populations of large unilamellar vesicles (LUV) and small multilamellar vesicles. The average particle sizes of the two vesicle types were the same. The SMV were formed from numerous lamellae (typcially 6–9) arranged in concentric rings inside the particle core, such that the innermost structures exhibit diameters as small as 20 nm. In general the encapsulated membrane structure are closely associated, however, many of the particles share a common feature where the outer 2–4 lamellae at one side of the particle appear to separate. Interestingly, at the low ODN-to-lipid ratio, the particle are predominantly unilamellar, but exhibit a cap-like structure that may represent the interaction between two vesicles and could be a precursor to the SMV structures observed at the higher ODN-to-lipid ratios.

What is claimed is:

1. A composition comprising a population of oligodeoxynucleotide-containing lipid vesicles in an aqueous carrier, at least a portion of the lipid vesicles within said population being small multilamellar vesicles, wherein the small multilamellar vesicles comprise:
   (a) a lipid component comprising 20–30 mol % of an ionizable amino lipid, a steric barrier lipid and additional lipid components selected from among neutral lipids and sterols; and
   (b) oligodeoxynucleotides contained in the lumen or interlamellar spaces of the small multilamellar vesicles, wherein the ionizable lipid is selected from the group consisting of DODMA and DODAP.

2. The composition according to claim 1, wherein the oligodeoxynucleotide and the lipid component are present in a weight/weight ratio of from 0.025 to 0.25.

3. The composition according to claim 1, wherein the oligodeoxynucleotide and the lipid component are present in a weight/weight ratio of from 0.15 to 0.25.

4. The composition according to claim 1, wherein the oligodeoxynucleotide and the lipid component are present in a weight/weight ratio of from 0.015 to 0.20.

5. The composition according to claim 1, wherein the ionizable amino lipid is DODAP.

6. The composition according to claim 2, wherein the steric barrier lipid is PEG-CerC$_{14}$.

7. The composition according to claim 6, wherein the lipid component comprises a sterol, and the sterol is cholesterol.

8. The composition according to claim 6, wherein the lipid component comprises a neutral lipid selected from among DOPE, DSPC, POPC and, SM.

9. The composition according to claim 1, wherein the lipid component comprises DSPC, CHOL, DODAP and PEG-CerC$_{14}$ in a molar ratio of 25:45:20:10.

* * * * *

SEQUENCE LISTING (1) GENERAL INFORMATION:

(iii) NUMBER OF SEQUENCES: 17

(2) INFORMATION FOR SEQ ID NO: 1:

-continued

```
      (i) SEQUENCE CHARACTERISTICS:
          (A) LENGTH: 20
          (B) TYPE: nucleic acid
          (C) STRANDEDNESS: single
          (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 1:

TGCATCCCCC AGGCCACCAT                                                    20

(2) INFORMATION FOR SEQ ID NO: 2:

(i) SEQUENCE CHARACTERISTICS:
          (A) LENGTH: 20
          (B) TYPE: nucleic acid
          (C) STRANDEDNESS: single
          (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 2:

GCCCAAGCTG GCATCCGTCA                                                    20

(2) INFORMATION FOR SEQ ID NO: 3:

(i) SEQUENCE CHARACTERISTICS:
          (A) LENGTH: 15
          (B) TYPE: nucleic acid
          (C) STRANDEDNESS: single
          (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 3:

GGTGCTCACT GCGGC                                                         15

(2) INFORMATION FOR SEQ ID NO: 4:

(i) SEQUENCE CHARACTERISTICS:
          (A) LENGTH: 15
          (B) TYPE: nucleic acid
          (C) STRANDEDNESS: single
          (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 4:

AACGTTGAGG GGCAT                                                         15

(2) INFORMATION FOR SEQ ID NO: 5:

(i) SEQUENCE CHARACTERISTICS:
          (A) LENGTH: 16
          (B) TYPE: nucleic acid
```

```
        (C) STRANDEDNESS: single
        (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 5:

TAACGTTGAG GGGCAT                                                    16

(2) INFORMATION FOR SEQ ID NO: 6:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 6:

TATGCTGTGC CGGGGTCTTC GGGC                                           24

(2) INFORMATION FOR SEQ ID NO: 7:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 7:

GTGCCGGGGT CTTCGGGC                                                  18

(2) INFORMATION FOR SEQ ID NO: 8:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 8:

GGACCCTCCT CCGGAGCC                                                  18

(2) INFORMATION FOR SEQ ID NO: 9:

(i) SEQUENCE CHARACTERISTICS:
        (A) LENGTH: 18
        (B) TYPE: nucleic acid
        (C) STRANDEDNESS: single
        (D) TOPOLOGY: linear
```

(ii) MOLECULE TYPE: other nucleic acid (iii) HYPOTHETICAL: no (iv) ANTI-SENSE: yes (xi) SEQUENCE DESCRIPTION: SEQ ID NO: 9:

TCCTCCGGAG CCAGACTT                                              18

(2) INFORMATION FOR SEQ ID NO: 10:

(i) SEQUENCE CHARACTERISTICS:
        (A) LENGTH: 15
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 10:

CCGTGGTCAT GCTCC                                                 15

(2) INFORMATION FOR SEQ ID NO: 11:

(i) SEQUENCE CHARACTERISTICS:
        (A) LENGTH: 21
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 11:

CAGCCTGGCT CACCGCCTTG G                                          21

(2) INFORMATION FOR SEQ ID NO: 12:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 12:

CAGCCATGGT TCCCCCCAAC                                            20

(2) INFORMATION FOR SEQ ID NO: 13:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 13:

GTTCTCGCTG GTGAGTTTCA                                                       20

(2) INFORMATION FOR SEQ ID NO: 14:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 14:

TCTCCCAGCG TGCGCCAT                                                         18

(2) INFORMATION FOR SEQ ID NO: 15:

(i) SEQUENCE CHARACTERISTICS:
        (A) LENGTH: 15
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 15:

GTGCTCCATT GATGC                                                            15

(2) INFORMATION FOR SEQ ID NO: 16:

(i) SEQUENCE CHARACTERISTICS:
        (A) LENGTH: 34
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 16:

GAGUUGCUGA UGAGGCCGAA AGGCCGAAAG UCUG                                        34

(2) INFORMATION FOR SEQ ID NO: 17:

(i) SEQUENCE CHARACTERISTICS:
        (A) LENGTH: 15
        (B) TYPE: nucleic acid
        (C) STRANDEDNESS: single
        (D) TOPOLOGY: linear (ii) MOLECULE TYPE: other nucleic acid (iii) HYPOTHETICAL: no

```
    (iv) ANTI-SENSE: y (xi) SEQUENCE DESCRIPTION: SEQ ID NO: 17:

GAACGGAGAC GGTTT                                                15
```